United States Patent
Cook et al.

(10) Patent No.: US 10,744,184 B2
(45) Date of Patent: Aug. 18, 2020

(54) FGF-23 EPITOPE PEPTIDES AND METHODS OF USE THEREOF

(71) Applicant: Wisconsin Alumni Research Foundation, Madison, WI (US)

(72) Inventors: Mark E. Cook, Madison, WI (US); Elizabeth A. Bobeck, Baraboo, WI (US); Kimberly S. Burgess, Ames, IA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/623,450

(22) Filed: Jun. 15, 2017

(65) Prior Publication Data
US 2017/0281741 A1 Oct. 5, 2017

Related U.S. Application Data

(62) Division of application No. 14/735,648, filed on Jun. 10, 2015, now Pat. No. 9,708,369, which is a division of application No. 13/661,571, filed on Oct. 26, 2012, now Pat. No. 9,078,842.

(60) Provisional application No. 61/551,749, filed on Oct. 26, 2011.

(51) Int. Cl.
| | |
|---|---|
| A61K 38/18 | (2006.01) |
| C07K 16/22 | (2006.01) |
| C07K 14/50 | (2006.01) |
| A61K 47/64 | (2017.01) |
| A61K 39/00 | (2006.01) |
| C07K 7/06 | (2006.01) |
| A61K 39/385 | (2006.01) |

(52) U.S. Cl.
CPC .......... *A61K 38/1825* (2013.01); *A61K 39/00* (2013.01); *A61K 39/385* (2013.01); *A61K 47/646* (2017.08); *C07K 7/06* (2013.01); *C07K 14/50* (2013.01); *C07K 16/22* (2013.01); *A61K 2039/54* (2013.01); *A61K 2039/552* (2013.01); *A61K 2039/575* (2013.01); *A61K 2039/58* (2013.01); *A61K 2039/6031* (2013.01); *A61K 2039/6081* (2013.01)

(58) Field of Classification Search
None
See application file for complete search history.

(56) References Cited

U.S. PATENT DOCUMENTS 5,846,547 A 12/1998 Cleary
7,094,551 B2 8/2006 Zahradnik et al.

OTHER PUBLICATIONS

Biehl et al., "Activity of various hydroxylated vitamin D3 analogs for improving phosphorus utilisation in chicks receiving diets adequate in vitamin D3," British Poultry Science, 1998, vol. 39, pp. 408-412.
Bobeck et al.. "Maternally-derived antibody to fibroblast growth factor-23 reduced dietary phosphate requirements in growing chicks", Biochemical and Biophysical Research Communications, 2012, vol. 420, pp. 666-670.
Carter, "Chapter 10—Techniques for Conjugation of Synthetic Peptides to Carrier Molecules," Methods in Molecular Biology, vol. 36: Peptide Analysis Protocols, 1994, pp. 155-191.
Carter, "Conjugation of Peptides to Carrier Proteins via Glutaraldehyde", The Protein Protocols Handbook, 1996, pp. 679-687.
Cook et al., "IgY-Immune component of eggs as a source of passive immunity for animals and humans," World's Poultry Science Journal, Jun. 2010, vol. 66, pp. 215-226.
Cooper, P.D., "Chapter 9—The Selective Induction of Different Immune Responses by Vaccine Adjuvants," Strategies in Vaccine Design, G.L. Ada, ed. R.G. Landes Company, Austin, TX, 1994, pp. 125-158.
Liu et al., "Emerging role of fibroblast growth factor 23 in a bone-kidney axis regulating systemic phosphate homeostasis and extracellular matrix mineralization," Curr. Opin. Nephrol. Hypertens., 2007, vol. 16. pp. 329-335.
Liu et al., "How Fibroblast Growth Factor 23 works," J. Am. Soc. Nephrol., 2007, vol. 18, pp. 1637-1647.
Sommerville et al., "The Time Sequence of Adaptive Changes to Dietary Phosphorus Deficiency in the Chick," Horm. Metabol. Res., 1985, vol. 17, pp. 247-250.
Stubbs et al., "Role of Fibroblast Growth Factor 23 in Phosphate Homeostasis and Pathogenesis of Disordered Mineral Metabolosm in Chronic Kidney Disease," Seminars in Dialysis, 2007, vol. 20, No. 4, pp. 302-308.
Ward, "Phosphorus-friendly transgenics," Nature Biotechnology, May 2001, vol. 19, pp. 415-416.
Yamashita et al., "Identification of a Novel Fibroblast Growth Factor, FGF-23, Preferentially Expressed in the Ventrolateral Thalamic Nucleus of the Brain," Biochem. Biophys. Res. Commun. 277, 2000, pp. 494-498.
Biehl et al., "Activity of various hydroxylated vitamin D3 analogs for improving phosphorus utilisation in chicks receiving diets adequate in vitamin D3," British Poultry Science, 39:408-412 (1998).
Cook and Trott, "IgY-Immune component of eggs as a source of passive immunity for animals and humans," World's Poultry Science Journal 66:215-226 (2010).

*Primary Examiner* — Christine J Saoud
(74) *Attorney, Agent, or Firm* — Cantor Colburn LLP

(57) ABSTRACT

Disclosed are methods of altering metabolism of phosphate in a livestock via an antibody. The methods involve the development of an antibody against FGF-23 for the purpose of reducing phosphate excretion by an animal.

14 Claims, 12 Drawing Sheets
Specification includes a Sequence Listing.

FGF-23 EPITOPE PEPTIDES AND METHODS OF USE THEREOF

CROSS-REFERENCE TO RELATED APPLICATION

This application is a divisional of U.S. application Ser. No. 14/735,648, filed on Jun. 10, 2015, which is a divisional of U.S. application Ser. No. 13/661,571, filed on Oct. 26, 2012, now U.S. Pat. No. 9,078,842, which claim priority to U.S. Provisional Patent Application No. 61/551,749, filed Oct. 26, 2011, which are incorporated herein by reference in their entirety.

INCORPORATION OF SEQUENCE LISTING

A paper copy of the Sequence Listing and a computer readable form of the sequence containing the file named "WIS0039USD2 sequence listing_ST25.TXT", which is 9 kb in size, are provided herein and are herein incorporated by reference. This Sequence Listing consists of SEQ ID NOS:1-48.

BACKGROUND OF THE DISCLOSURE

The present disclosure relates generally to a method of altering metabolism of a dietary nutrient (e.g., phosphate) in livestock via an antibody, which increases the absorption and retention of the dietary nutrient, thereby decreasing its excretion into the environment.

Fibroblast growth factor-23 (FGF-23) has recently been identified as a major player in phosphate homeostasis. (See Liu and Quarles, "How Fibroblast Growth Factor 23 works," J. Am. Soc. Nephrol. 18:1637-1647 (2007) and Yamashita et al., "Identification of a novel fibroblast growth factor, FGF-23, preferentially expressed in the ventrolateral thalamic nucleus of the brain," Biochem. Biophys. Res. Commun. 277:494-498 (2000)). FGF-23 is predominately produced by osteocytes in bone, and its principal actions are to inhibit sodium-dependent phosphate reabsorption and 1α-hydroxylase activity in the kidney, leading to increased phosphate excretion and low circulating 1,25(OH)$_2$D$_3$ levels (hence reduced intestinal absorption of phosphate). (See Liu and Quarles, "How Fibroblast Growth Factor 23 works," J. Am. Soc. Nephrol. 18:1637-1647 (2007) and Liu et al., "Emerging role of fibroblast growth factor 23 in a bone-kidney axis regulating systemic phosphate homeostasis and extracellular matrix mineralization," Curr. Opin. Nephrol. Hypertens. 16:329-335 (2007)). It has been suggested that FGF-23 behaves as a counter regulatory hormone for 1,25(OH)$_2$D$_3$, which maintains phosphate balance in the presence of vitamin D-mediated suppression of parathyroid hormone and increased intestinal phosphate and calcium absorption. Low levels of FGF-23 are detected in circulation in normal individuals; however, levels are increased in response to phosphate loading, vitamin D administration, renal failure, and in hereditary and acquired hypophosphate homeostasis and mineralization. (See Liu and Quarles, "How Fibroblast Growth Factor 23 works," J. Am. Soc. Nephrol. 18:1637-1647 (2007) and Stubbs et al., "Role of Fibroblast Growth Factor 23 in Phosphate Homeostasis and Pathogenesis of Disordered Mineral Metabolosm in Chronic Kidney Disease," Seminars in Dialysis 20:302-308 (2007)).

Phosphate homeostasis and excretion is of particular interest in agriculture. Phosphate is typically fed above the animal's requirement to promote growth in an animal, particularly a livestock. Circulatory phosphate levels above the immediate needs of the animal are rapidly excreted by action of FGF-23. Not only is excess phosphate that is excreted by the animal an environmental concern but excreted phosphate is also costly to the producer because of the high cost of phosphate supplements used for animal growth. Discovery of means to improve the retention of phosphate by the animal would decrease the need to add expensive phosphate to the animal's diet and would reduce phosphate contamination of the environment from animal excreta. (See Ward, "Phosphorus-friendly transgenics," Nature Biotechnology, 19:415-416 (2001)).

Accordingly, there is a need for methods of altering the metabolism of dietary phosphate in animals such to increase phosphate availability and absorption, thereby reducing the amount of phosphate required for administration in animals.

BRIEF DESCRIPTION OF THE DISCLOSURE

Briefly, the present disclosure is directed to an isolated polypeptide comprising an amino acid sequence having at least 75% sequence identity to an amino acid sequence selected from the group consisting of SEQ ID NO:1, SEQ ID NO:2, SEQ ID NO:3, SEQ ID NO:4, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

In another embodiment, the present disclosure is directed to a vaccine comprising a polypeptide and a carrier protein. The polypeptide comprises an amino acid sequence having at least 75% sequence identity to an amino acid sequence selected from the group consisting of SEQ ID NO:1, SEQ ID NO:2, SEQ ID NO:3, SEQ ID NO:4, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

In another embodiment, the present disclosure is directed to a method of eliciting an immune response in a livestock. The method comprises introducing into the livestock a polypeptide, wherein the polypeptide comprises an amino acid sequence having at least 75% sequence identity to an amino acid sequence selected from the group consisting of SEQ ID NO:1, SEQ ID NO:2, SEQ ID NO:3, SEQ ID NO:4, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

In yet another embodiment, the present disclosure is directed to a method of altering metabolism of a dietary nutrient in a livestock offspring. The method comprises inducing production of a maternal antibody by introducing a polypeptide into a fertile livestock female, wherein the polypeptide comprises an amino acid sequence having at least 75% sequence identity to an amino acid sequence selected from the group consisting of SEQ ID NO:1, SEQ ID NO:2, SEQ ID NO:3, SEQ ID NO:4, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45, and fertilizing at least one gamete of the livestock, wherein said maternal antibody is transferred via egg yolk, through the placenta, or via colostrum to the livestock offspring, thereby altering the livestock offspring's metabolism of the dietary nutrient.

In another embodiment, the present disclosure is directed to a method of altering phosphate metabolism in a livestock, the method comprising inducing production of an antibody by introducing a polypeptide into the livestock, wherein said antibody inhibits the action of FGF-23.

BRIEF DESCRIPTION OF THE DRAWINGS

As shown in FIG. 1A, * denotes significant difference between low (Lpi) and normal (Npi) dietary phosphate within antibody treatment. As shown in FIGS. 1B and 1C, differing letters denote significant difference between low and normal phosphate within antibody treatment. FCA is control antibody; FGF-1 is antibody to SEQ ID NO: 1.

As shown in FIGS. 2B and 2C, differing letters denote significant difference between low and normal phosphate within antibody treatment. FCA is control antibody; FGF-1 is antibody to SEQ ID NO: 5.

DETAILED DESCRIPTION OF THE DISCLOSURE

Figure 1A:
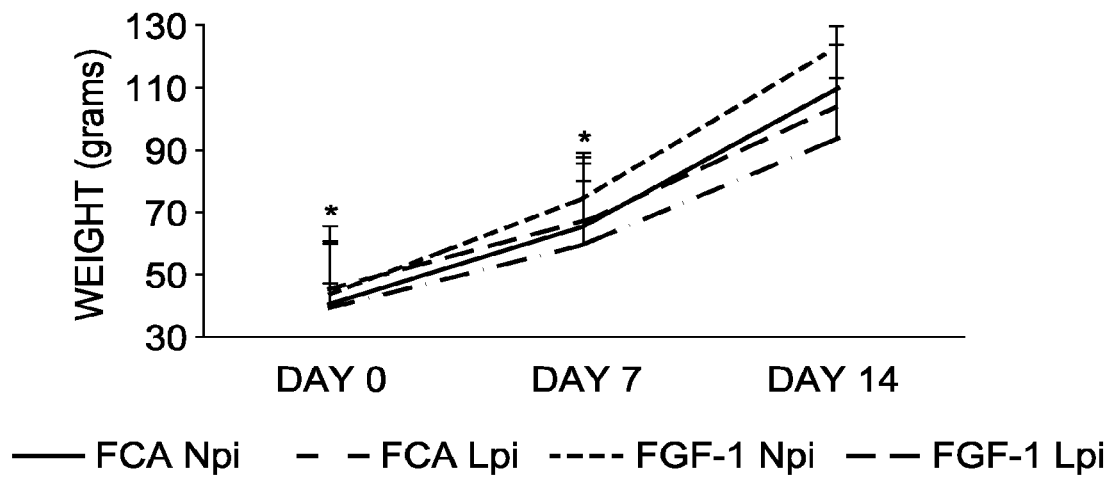
FIGS. 1A, 1B, and 1C are graphs depicting, respectively, weight, plasma phosphate, and bone ash results of passive anti-FGF-23 (FGF-1; SEQ ID NO: 1) chicks at the conclusion of a two week trial with each group on either an adequate or deficient phosphate diet as analyzed in Example 1.

The present disclosure is therefore directed to a method for reducing the amount of a dietary nutrient, e.g., phosphate, required in a livestock diet. The method involves the development of an antibody against one of the key molecules that promotes excretion of phosphate, FGF-23. According to some aspects of the present disclosure, this antibody could be induced in the animal directly through vaccination. According to some aspects of the present disclosure, this antibody could be maternally derived, i.e., a maternal antibody, which is transferred to the offspring. As used herein, the term "maternal antibody" refers to an antibody produced during an immune response in a mother. Livestock whose diets may be altered according to the methods of the present disclosure include avian (including chicken, turkey, duck, goose, peafowl, emu, pheasant, guinea, fowl, quail, among others), swine, sheep, cattle, and fish. For example, avian are suitable for the method of the present disclosure since, in some embodiments, the method involves the transfer of a maternal antibody to offspring. Avian maternally transfer protective antibodies via the yolk of fertilized eggs and the fertile embryo takes these maternal antibodies up during incubation. (See Cook and Trott, "IgY-Immune component of eggs as a source of passive immunity for animals and humans," World's Poultry Science Journal 66:215-226 (2010)). Industry has already successfully used hen egg antibodies to alter inflammatory processes and promote growth in livestock. Fish maternal transfer is similar to avian, where transfer occurs via the egg yolk. The transfer of maternal antibody to the offspring of species such as sheep, cattle and swine also occurs, however this transfer occurs during the first suckling period after birth, where the maternal antibody is transferred through the placenta and from the first milk (colostrum) to circulation by way of an "open gut." In one embodiment, the present disclosure is therefore directed to a method of neutralization of FGF-23 using maternally transferred antibody altered dietary phosphate requirements using an established chick growth model. (See Biehl et al., "Activity of various hydroxylated vitamin D3 analogs for improving phosphorus utilisation in chicks receiving diets adequate in vitamin D3," British Poultry Science, 39:408-412 (1998)).

The methods of the present disclosure alter the metabolism of a dietary nutrient, e.g., phosphate, in a livestock offspring via an antibody-based method in which a fertile female livestock (e.g., a laying hen) is vaccinated with vaccine comprising an FGF-23 peptide. This peptide is based on an epitopic analysis of FGF-23. In general, according to the methods of the present disclosure, the anti-FGF-23 peptide is injected into a fertile female livestock (e.g., a laying hen) to confer antibodies to the fertile eggs or offspring. The offspring, e.g., chicks, with the acquired antibodies have a decreased FGF-23 response when fed a diet comprising phosphate, thereby causing more phosphate to be absorbed in the intestine and enhanced resorption in the renal system. This in turn reduces the amount of phosphate needed in their diet and the amount of phosphate excreted in their waste.

According to another aspect of the present disclosure, a vaccine is provided for controlling the dietary phosphate requirements of livestock. The vaccine comprises an FGF-23 peptide. The vaccine may be used as part of a vaccination regimen for controlling phosphate dietary requirements in livestock, particularly chickens, swine, sheep, cattle, and fish, optionally in combination with vaccinations for the protection against disease. Commercial poultry are typically vaccinated to protect them against a variety of diseases including: Marek's disease, Newcastle disease, fowl pox, and avian encephalomyelitis. The vaccine of the present disclosure may be administered as part of the regimen used by commercial poultry producers and could be properly timed such that both maternal antibody transfer plus the individual's own response to a vaccine directly administered to the individual assure continued circulating levels of antibody to FGF-23 throughout the life of the animal.

According to yet another aspect of the present disclosure, the method of transferring maternal anti-FGF-23 antibodies to livestock offspring may be used in combination with current technologies for meeting the phosphate requirements of livestock including inorganic phosphate dietary supplementation, phytase supplementation for breaking down phytate phosphate (the form of phosphate present in plant tissues, e.g., corn and soy) for increased absorption, citric acid supplementation for increasing phytate digestibility, and $1,25(OH)_2D_3$ supplementation to increase phosphate availability and absorption through the up-regulation of the sodium phosphate transporter 2B. Inorganic phosphate and phytase are the most commonly used. While these supplements address the issue of available phosphate, they do not influence phosphate retention or absorption. The FGF-23 vaccine could be used in combination with these existing solutions to improve their efficacy. Ultimately, the present disclosure could significantly reduce or eliminate the amount of phosphate fed to livestock, and reduce the amount of phosphate excreted by the animal, providing environmental and economic benefits.

The methods of the present disclosure include inducing the production of antibodies to epitopes of the FGF-23 peptide (i.e., anti-FGF-23 antibodies), which in some embodiments, may be passively transferred to an offspring. The anti-FGF-23 antibodies block the mechanism by which FGF-23 increases the urinary excretion of phosphate. FGF-23 is secreted by osteocytes/osteoblasts in bone and connective tissue and is released into the plasma in response to an increase in plasma phosphate, Pi, concentration. FGF-23 acts in the kidney, in that it inhibits renal reabsorption of phosphate in the kidney, mostly in the proximal convoluted tubule. FGF-23 also inhibits 1-hydroxylase. 1-hydroxylase is responsible for the conversion of calcidiol to calcitriol (the biologically active form of vitamin D, which enhances intestinal phosphate absorption).

"Antibody" (Ab) and "antibodies" (Abs) refer to monoclonal antibodies (mAb (singular) or mAbs (plural)), polyclonal antibodies (pAbs (plural)), multispecific antibodies, recombinant antibodies, chimeric antibodies (cAb; a polypeptide comprising all or a part of the heavy and light chain variable regions of an antibody from one host species linked to at least part of the antibody constant regions from another host species), single chain antibodies, single domain antibodies, Fab fragments, F(ab') fragments, Fab'-SH fragments, $F(ab)_2$ fragments, Fd fragments, Fv fragments, single-chain Fv fragments ("scFv"), disulfide-linked Fv fragments ("sdFv"), an isolated complementarity determining region (CDR), and anti-idiotypic ("anti-Id") antibodies, and functionally active, epitope-binding fragments (or antigenically reactive fragments) of any of the above. Immunoglobulin molecules can be of any type (for example, IgG, IgE, IgM, IgD, IgA and IgY), class (for example, IgG1, IgG2, IgG3, IgG4, IgA1 and IgA2), or subclass. Antibodies to the peptides disclosed herein for use in the context of the present disclosure may be made using a variety of different techniques known in the art. For example, polyclonal and monoclonal antibodies may be raised by immunizing a suitable subject (such as, for example, a rabbit, goat, mouse or other mammal) with an immunogenic preparation that contains a suitable immunogen. The immunogen may be enriched/purified and isolated from a cell that produces it using affinity chromatography, immunoprecipitation or other techniques that are well known in the art. Alternatively, immunogen may be prepared using chemical synthesis using routine techniques known in the art (such as, for example, a synthesizer). The antibodies raised in the subject may then be screened to determine if the antibodies bind to the immunogen (or a fragment thereof, a variant thereof, or a fragment of a variant thereof).

The structures of chicken FGF-23, human FGF-23, pig FGF-23, cow FGF-23, and fish FGF-23 were studied, and multiple epitopes comprising oligopeptides sequences were identified, sequenced, and synthesized. Sequences were retrieved, aligned, and compared for homology using a commercial database, e.g., UniProtKB protein database (human, chick, etc). Sequences may be analyzed for antigenicity, e.g., using the Markov model and/or propensity scale methods. Specifically, the sequences may be analyzed for antigenicity using the BepiPred 1.0 server and the EPCES server to determine antigenicity (two separate prediction engines for likelihood to cause antibody production). Protein structure may also be determined using a commercial database, e.g., the PDBe database (3-dimensional protein structure database). A combination of the information derived from UniProtKB, antigen prediction servers, and 3D structure, enables determination and selection of sequences having desired properties, including, hydrophilicity, homology between species, and accessibility on the FGF-23 protein molecule. Once suitable sequences are selected, the peptides may be synthesized without modifications and with sufficient purity, such as <98% purity in milligram quantities by Genscript (Piscataway, N.J.).

According to some embodiments the oligopeptide epitope sequences include an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and SEQ ID NO:48. These epitopes have the sequences as shown in Table 1:

TABLE 1 oligopeptide epitope sequences.

| SEQ ID NO: | Peptide Sequence | Description of FGF-23 Epitope |
|---|---|---|
| 1 | VDGAPHQT | Human FGF-1 |
| 2 | INGVPHQT | Chicken FGF-1 |
| 3 | VDGSPQQT | FGF-1 (Pig and Cow) |
| 4 | VRKSTART | Fish FGF-1 |
| 5 | TLENGYDV | FGF-U (Human, Chicken, Pig, and Cow) |
| 6 | LLENNRDV | Fish FGF-U |
| 7 | YPNASPLL | Human FGF-2 |
| 8 | FPNSSPLL | Chicken FGF-2 |
| 9 | YPDTSPLL | Pig FGF-2 |
| 10 | YPNSSPLL | Cow FGF-2 |
| 11 | APNASPLV | Fish FGF-2 |
| 12 | AFLPGMNP | Human FGF-3 |
| 13 | VFFPGMNP | Chicken FGF-3 |
| 14 | AFLPGTNP | FGF-3 (Pig and Cow) |
| 15 | VFVVGQNV | Fish FGF-3 |
| 16 | RDPLNVLK | Human W |
| 17 | LDPHQILV | Chicken W |
| 18 | GDPLSVLK | W (Pig and Cow) |
| 19 | SDPHRVAV | Fish W |
| 20 | RRHTRSAE | Human T |
| 21 | HRNTRSAD | Chicken T |
| 22 | RRHTRSAH | Pig T |
| 23 | RRHTRSAH | Cow T |
| 24 | HRDKRNQV | Fish T |
| 25 | GMNPPPYS | NP-1 (Human and Chicken) |
| 26 | GTNPPPYA | NP-1 (Pig and Cow) |
| 27 | GQNVPQTS | Fish NP-1 |
| 28 | RNEIPLIH | Human NP-2 |
| 29 | RNEIPLFR | Chicken NP-2 |
| 30 | RNEIPLLH | Pig NP-2 |
| 31 | RNEIPLPH | Cow NP-2 |
| 32 | TNTVPLER | Fish NP-2 |
| 33 | AKRAFLPG | NP-3 (Human, Pig, and Cow) |
| 34 | TKQVFFPG | Chicken NP-3 |
| 35 | SRQVFVVG | Fish NP-3 |
| 36 | NTPIPRR | Human NP-4 |
| 37 | FNTPEPHR | Chicken NP-4 |
| 38 | ATARPRR | Pig NP-4 |
| 39 | AATARPRR | Cow NP-4 |
| 40 | LLHR | Fish NP-4 |
| 41 | TRSAEDDS | Human NP-5 |
| 42 | TRSADVDP | Chicken NP-5 |
| 43 | TRSAHDGG | Pig NP-5 |

TABLE 1-continued oligopeptide epitope sequences.

| SEQ ID NO: | Peptide Sequence | Description of FGF-23 Epitope |
|---|---|---|
| 44 | TRSAHDSG | Cow NP-5 |
| 45 | KRNQVVDP | Fish NP-5 |
| 46 | QTIYSALMI | FGF-C (Human, Chicken, and Pig) |
| 47 | QTVYSALMI | Cow FGF-C |
| 48 | RTSYSVILL | Fish FGF-C |

The present disclosure encompasses the oligopeptide epitope sequences listed in Table 1 and epitope sequences of substantial homology. According to some embodiments, three amino acids may be changed such that the oligopeptide epitope sequence has 60% sequence identity to an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:37, SEQ ID NO:39, SEQ ID NO:41, SEQ ID NO:42, SEQ ID NO:43, SEQ ID NO:44, SEQ ID NO:45, SEQ ID NO:46, SEQ ID NO:47, and SEQ ID NO:48. According to some embodiments, two amino acids may be changed such that the oligopeptide epitope sequence has 75% sequence identity to an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:37, SEQ ID NO:39, SEQ ID NO:41, SEQ ID NO:42, SEQ ID NO:43, SEQ ID NO:44, SEQ ID NO:45, and SEQ ID NO:46, SEQ ID NO:47, and SEQ ID NO:48. According to some embodiments, one amino acid may be changed such that the oligopeptide epitope sequence has about 85% sequence identity to an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, SEQ ID NO:46, SEQ ID NO:47, and SEQ ID NO:48. According to some embodiments, the oligopeptide epitope sequence is an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and SEQ ID NO:48.

Techniques for determining amino acid sequence "identity" are well known in the art. In general, "identity" means the exact amino acid to amino acid comparison of two or more polypeptides at the appropriate place, where amino acids are identical or possess similar chemical and/or physical properties such as charge or hydrophobicity. A so-termed "percent identity" may then be determined between the compared polypeptide sequences. Techniques for determining amino acid sequence identity also are well known in the art and include determining the nucleotide sequence of the mRNA for that gene (usually via a cDNA intermediate) and determining the amino acid sequence encoded therein, and comparing this to a second amino acid sequence. Two or more amino acid sequences can be compared by determining their "percent identity" or "percent sequence identity". The programs available, for example, the Wisconsin Sequence Analysis Package, Version 8 (available from Genetics Computer Group, Madison, Wis.) and the GAP program, are capable of calculating the identity between two polypeptide sequences. Other programs for calculating identity between sequences are known by those skilled in the art.

The FGF-23 oligopeptide epitope sequences may be used in the preparation of conjugate vaccines. According to some embodiments of the present disclosure, the isolated epitope may be conjugated with a carrier protein and formulated into a vaccine. Suitable carrier proteins include bovine gamma globulin, FGF-23, bovine serum albumin, keyhole limpet hemocyanin, ovalbumin, or any protein that, when conjugated with the peptide, elicits an antibody to the attached peptide. According to some embodiments, the epitope may belong to a species other than the livestock species, e.g., a human FGF-23 oligopeptide epitope, and the carrier protein may be endogenous FGF-23. According to some embodiments, the entire sequence of FGF-23 could be used as a vaccine without conjugation.

The epitope sequence may be conjugated according to methods known in the art. In some embodiments, the epitope sequence may be conjugated to the carrier protein via a glutaraldehyde linking moiety. In some embodiments, the epitope sequence may be conjugated to the carrier protein via maleimide mediated conjugation. In some embodiments, the epitope sequence may be conjugated via 1-Ethyl-3-[3-dimethylaminopropyl]carbodiimide hydrochloride (EDC) mediated conjugation. Other methods of hatpen-carrier protein conjugations could be used and the method of conjugation is not critical as long as antibody to the desired peptide is effectively generated (see Carter, Techniques for conjugation of synthetic peptides to carrier molecules, Methods Molecular Biology 36:155-191 (1994); Carter, Conjugation of peptides to carrier proteins via glutaraldehyde pp 679-687, In Protein Protocols Handbook, eds J. M. Walker, Humana Press, Totowa, N.J.).

The conjugate vaccine comprising the FGF-23 epitope sequence and carrier protein is prepared in an immunopotentiator, specifically an immunological adjuvant. Suitable adjuvants for preparing a conjugate vaccine according to the present disclosure include alum, aluminum phosphate, aluminum hydroxide, squalene, and oil-based adjuvants including Freund's Complete and Incomplete adjuvant or others as listed in Cooper, P. D. (The selective induction of different immune responses by vaccine adjuvants; Strategies in Vaccine Design. G. L. Ada, ed. R. G. Landes Company, Austin, Tex. (1994)). A specific adjuvant suitable for preparing the conjugate vaccine according to the present disclosure is Freund's complete adjuvant. Another specific adjuvant suitable for preparing the conjugate vaccine according to the present disclosure is Freund's incomplete adjuvant. Branded commercial adjuvants are also available and are suitable such as, for example, Titermax, AddaVax, Alhydrogel. In general, the concentration of the conjugated vaccine in the adjuvant formulation generally ranges from about 50 micrograms to about 6 milligrams, preferably between about 50 micrograms and about 3 milligrams, even more preferably between about 50 micrograms and about 1 milligram.

According to some methods of the present disclosure, a maternal livestock, e.g., a laying hen, is injected with the conjugate vaccine comprising the FGF-23 oligopeptide epitope sequence conjugated to a carrier protein. The conjugate vaccine may be carried in an adjuvant, e.g., Freund's complete adjuvant. In some embodiments, the maternal livestock may be vaccinated in combination with a conventional vaccination regimen. Injections may occur once or multiple times, e.g., a secondary booster shot injected about one to two weeks after the primary vaccination. The secondary booster shot may comprise the same adjuvant or a different adjuvant, e.g., Freund's incomplete adjuvant.

The vaccination elicits an immune system response, which results in the production of antibodies against an endogenous protein, specifically, antibodies against endogenous FGF-23. The maternal livestock's (e.g., laying hen) immune system recognizes the epitopes, which mobilizes the preparation of maternal antibodies that recognize the FGF-23 oligopeptide epitope sequence. In some embodiments, the epitopes comprise FGF-1, human and chicken FGF-3, W, human and chicken T, and/or FGF-U, whose structures are provided above.

According to the methods of the present disclosure, the maternal antibodies are transferred to the offspring. In some embodiments, the maternal livestock is poultry, e.g., a laying hen or fish, and the maternal antibodies are transferred via the egg yolk. The fertilized embryo assumes the maternal antibodies during incubation. Maternal antibodies may be acquired from swine, sheep and cattle, wherein the maternal antibodies are acquired through the placenta or orally from colostrum. According to some embodiments, the passively transferred maternal antibodies alter or block the function of an endogenous protein, thereby altering the metabolism of a dietary nutrient in the offspring. In some preferred embodiments, the passively transferred maternal antibodies alter or block the function of FGF-23 in the offspring, thereby decreasing the excretion of phosphate from the renal system and increasing the absorption of phosphate from the intestinal lumen. Without being bound by theory, is currently believed that the passively transferred maternal antibodies block the function of FGF-23 by binding thereto. The plasma concentration of FGF-23 in the normal, fasting state is generally low. The plasma concentration increases via the release from bone osteocytes in response to a meal comprising phosphate. The passively transferred maternal antibodies bind to FGF-23 in the blood plasma, thereby inhibiting its renal function. These effects enable feeding the livestock offspring, e.g., a chick, a diet having decreased phosphate concentration. In some embodiments, the amount of phosphate in the diet may be decreased at least 10 wt. %, at least 25 wt. %, or even at least 50 wt. %, and the growing chicks achieve weight and bone densities comparable to chicks receiving a diet comprising phosphate concentrations conventional in the industry.

In some embodiments, the vaccine including the FGF-23 oligopeptide epitope sequence conjugated to a carrier protein may be directly injected into livestock to induce active immunity. Particularly, an immune response in the livestock is elicited by introducing the vaccine into the livestock. The initial administration can be followed by one or more booster administrations of the vaccine.

In some embodiments, anti-FGF-23 antibody may be isolated and administered to a livestock. Suitable methods for administering the antibody may be, for example, orally and parentally.

Certain technologies have been developed for meeting the phosphate requirements of farm animals. These include dietary inorganic phosphate, phytase for breaking down phytate phosphate to increase its availability for absorption, citric acid which increases phytate digestibility, and 1α, 25 $(OH)_2D_3$ or analogue which also increases phosphate availability and absorption through the up-regulation of the sodium phosphate transporter 2b. The vaccination method of the present disclosure may be used in combination with any or all of these technologies for meeting the phosphate requirements of livestock. Inorganic phosphate and phytase are widely used in animal agriculture. These supplements address the issue of available phosphate, but have no influence on phosphate retention, and just because it is available in the lumen of the intestine, it does not mean it will be absorbed. In fact, elevated FGF-23 will decrease phosphate absorption even if it is more available in the lumen. A method combining dietary inorganic phosphate, phytase, and the anti-FGF-23 antibodies described herein should improve the phosphate utilization in livestock, thereby enabling reduction in the amount of phosphate in the diet.

In some embodiments, the methods of the present disclosure may be used in combination with citric acid and vitamin D supplementation. The active vitamin D products not only improve phytate phosphate bioavailability, they also increase absorption. Active vitamin D could overcome the block in phosphate absorption caused by FGF-23, but it will not affect retention at the level of the kidney.

The following examples illustrate specific embodiments within the scope of the present disclosure. The examples are provided for the purpose of illustration and are not to be construed as limitations of the present disclosure.

EXAMPLES

Example 1

In this Example, the effect of altering the function of FGF-23 through maternally-derived antibody on the dietary phosphate requirements of baby chicks was analyzed.

Materials and Methods

Conjugation of Selected Peptide and Injection

Bovine gamma globulin, a carrier protein, was dissolved in 0.1 molar sodium acetate buffer (5 mg/1 mL). 0.02M Glutaraldehyde was then added to the selected peptide (0.13 mL per 1 mg peptide) and allotted 2-3 hours to conjugate. The reaction was stopped after an hour by the addition of 20 mg glycine (98%). Conjugated peptides were then dialyzed overnight in phosphate buffered saline solution at room temperature in 6000-8000 molecular weight dialysis tubing.

The dialyzed, conjugated peptides were split into two aliquots for primary and secondary booster vaccinations. The booster was stored in −80° C. freezer until use. Primary injection was prepared by emulsifying the peptide-carrier solution in Freund's complete adjuvant at a 1:1 ratio. The emulsified peptides were then put into 3-ml syringes with 21-gauge needles and laying hens were injected across four sites (breast and thigh muscle) with the vaccine to either an epitope of FGF-23 peptide (FGF-1 (SEQ ID NO:1) or U (SEQ ID NO:5)) or the FCA control. Hens were boosted one week after primary vaccination as described above except Freund's incomplete adjuvant was used to emulsify the selected peptide or as control.

Experimental Animals

Three weeks after the primary vaccination, control or FGF-23 injected hens were inseminated 1×/week for 2 weeks. Fertile eggs were collected and incubated for 3 weeks, and the resulting chicks were randomly placed on a phosphate deficient or adequate diet.

To evaluate growth rates, chick weights were recorded at day zero (hatch) and then weekly. At the conclusion, chicks were bled via cardiac puncture and then $CO_2$ euthanized. The right tibiotarsus was removed for dry, fat-free bone ash analysis. Blood samples were collected for plasma phosphate analysis.

Mixing Diet

Two diets were mixed to accommodate deficient and adequate phosphate levels, deficient in available inorganic phosphate and adequate in available inorganic phosphate. The compositions of these diets are shown in Table 2.

TABLE 2

Composition of Diets Adequate and Deficient in Phosphate, Pi

| Ingredient | Deficient Pi Diet (%) | Adequate Pi Diet (%) |
|---|---|---|
| Base Mix* | 96.6 | 96.6 |
| $CaCO_3$ | 0.48 | 0.96 |
| $KH_2PO_4$ | 0.6 | 1.20 |
| Sand | 2.32 | 1.24 |

| Base Mix* | g/100 g |
|---|---|
| Corn | 51.93 |
| Soy 48 (soybean meal 48% protein) | 40.50 |
| Corn Oil | 5.10 |
| CaCO3 | 1.35 |
| Salt | 0.41 |
| DL-Methionine | 0.20 |
| Vitamin-Mineral Mix | 0.51 |

*The deficient and adequate diets contained 0.52% and 0.66% total and 0.28 and 0.42 available phosphate (Pi), respectively.

Dry Fat-Free Bone Ash

Fat was removed from collected bones via ether extraction for 5 days. Bones were then ashed at 600° F. in a muffle furnace for 24 hours and ash was determined from bone weights pre- and post-ashing in the furnace.

Plasma Phosphate

Plasma samples were taken to the University of Wisconsin Veterinary Lab for phosphate analysis using a colorimetric method on a Hitachi autoanalyzer (Wisconsin Veterinary Diagnostic Laboratory, 445 Easterday Ln, Madison, Wis. 53706).

Statistical Analyses

Data were analyzed by analysis of variance as a 2×2 factorial with dietary phosphate and antibody type as main effects. Pairwise comparisons were made using least square differences even if interactions were not statistically different. Treatment means were considered different ifp=0.05 or less. Difference with p=0.1 or less were described as trends in the results.

Results and Discussion

Effects of Anti-FGF-23 on Growth

Figure 2A:
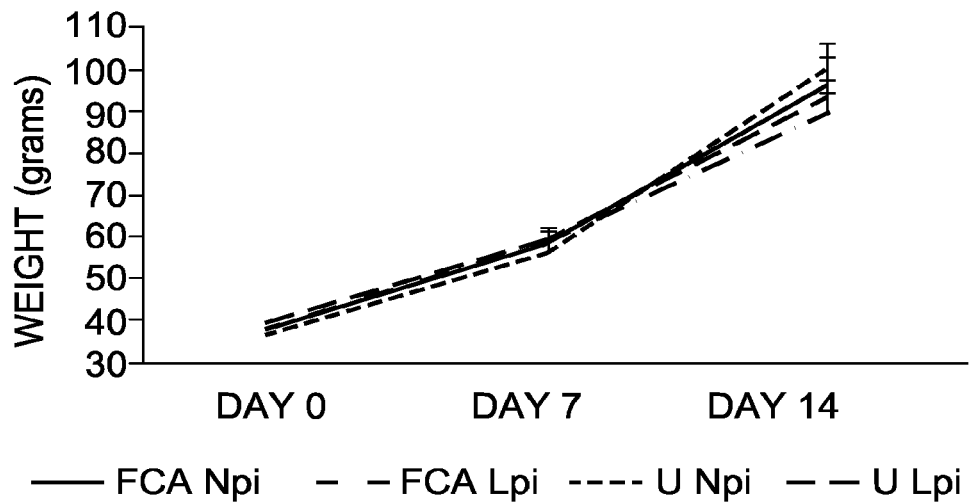
FIGS. 2A, 2B, and 2C are graphs depicting, respectively, weight, plasma phosphate, and bone ash results of passive anti-FGF-23 (FGF-U; SEQ ID NO: 5) chicks at the conclusion of a two week trial with each group on either an adequate (Npi) or deficient (Lpi) phosphate diet as analyzed in Example 1.

Chick weights of the treatment groups, over time are shown in FIGS. 1A, 2A, and Table 3. Feeding chicks a deficient diet resulted in a 15% decrease in final body weight (main effect of diet p<0.01) in experiment 1, but not in experiment 2 when compared to chicks fed an adequate phosphate diet. FGF-1 chicks had an 11% increase in final body weight (main effect of antibody p<0.09) when compared to the control antibody chicks in experiment 1, but not experiment 2. The decrease in body weight due to phosphate deficiency was prevented in deficient chicks receiving passive anti-FGF-1, such that their final body weight did not differ from the chicks fed adequate levels of dietary phosphate. Chicks with passive FGF-1 also had heavier body weights at hatch than chicks with control passive antibody. Passive antibody to FGF-U had no effect on weight at hatch.

The ability of anti-FGF-1 to overcome growth depression due to phosphate deficiency could be the result of the initial weight of chicks receiving passive antibody to FGF-23. It is well known in the literature that the heavier a chick is at hatch, the faster the growth rate. (See Sommerville et al., "The Time Sequence of Adaptive Changes to Dietary Phosphorus Deficiency in the Chick," Horm. Metabol. Res. 17:247-250 (1985)). Equally possible is that the neutralization of FGF-23 reduced the phosphate requirements of the baby chick by reducing urinary phosphate excretion and increasing intestinal phosphate absorption.

TABLE 3

Treatment means and p values for Experiment 1 and Experiment 2

| Trial No. | Anti-body | Diet | Weight (g) | | | Plasma Pi (mg/dL) | Bone Ash (g) |
|---|---|---|---|---|---|---|---|
| | | | Initial | Week 1 | Week 2 | | |
| 1 | FCA | Npi | $40.1^{bc}$ | $65.5^{ab}$ | $109.8^{ab}$ | $5.7^a$ | $0.128^{ab}$ |
| | | Lpi | $39.9^c$ | $59.6^b$ | $93.2^b$ | $3.0^b$ | $0.105^b$ |
| | FGF-1 | Npi | $43.6^{ab}$ | $74.3^a$ | $122.9^a$ | $6.0^a$ | $0.151^a$ |
| | | Lpi | $45.4^a$ | $67.3^{ab}$ | $104.0^{ab}$ | $3.8^b$ | $0.134^a$ |
| | SEM | | 1.0 | 3.1 | 6.6 | 0.4 | 0.01 |
| | P values | Diet | 0.68 | 0.05 | 0.01 | 0.01 | 0.07 |
| | | Ab | 0.01 | 0.02 | 0.09 | 0.22 | 0.02 |
| | | Diet × Ab | 0.22 | 0.87 | 0.87 | 0.52 | 0.77 |
| 2 | FCA | Npi | $38.7^{ab}$ | 59.1 | 96.3 | $5.1^a$ | $0.126^a$ |
| | | Lpi | $38.7^{ab}$ | 59.1 | 89.7 | $3.4^{bc}$ | $0.108^{ab}$ |
| | U | Npi | $36.7^b$ | 56.3 | 100.3 | $4.7^{ab}$ | $0.111^{ab}$ |
| | | Lpi | $40.1^a$ | 59.8 | 93.6 | $2.2^c$ | $0.097^b$ |
| | SEM | | 0.9 | 2.3 | 6.9 | 0.77 | 0.013 |
| | P values | Diet | 0.08 | 0.45 | 0.33 | 0.01 | 0.09 |
| | | Ab | 0.80 | 0.65 | 0.56 | 0.14 | 0.17 |
| | | Diet × Ab | 0.04 | 0.45 | 0.99 | 0.46 | 0.83 |

SEM = standard error of the mean,
Ab = antibody

Effects of Anti-FGF-23 on Plasma Phosphate Levels

Figure 1B:
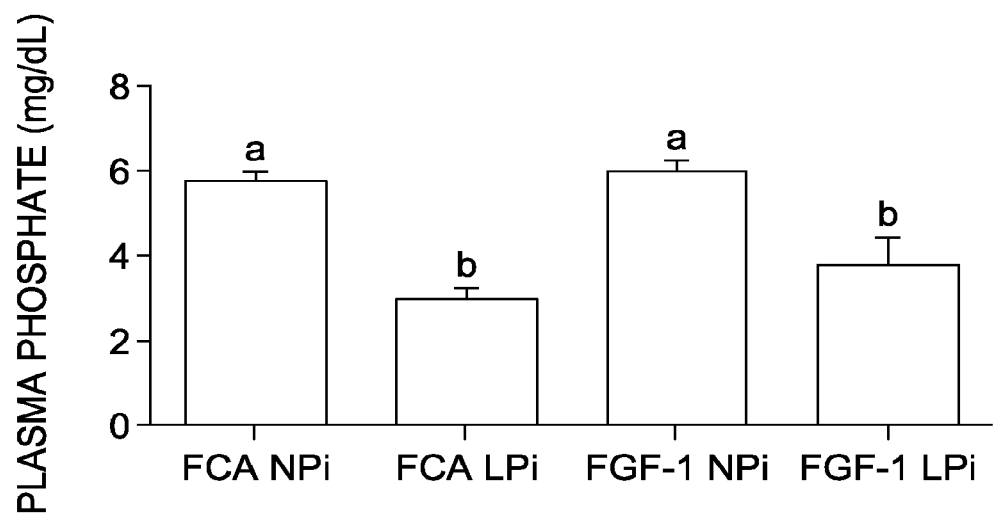
Figure 1C:
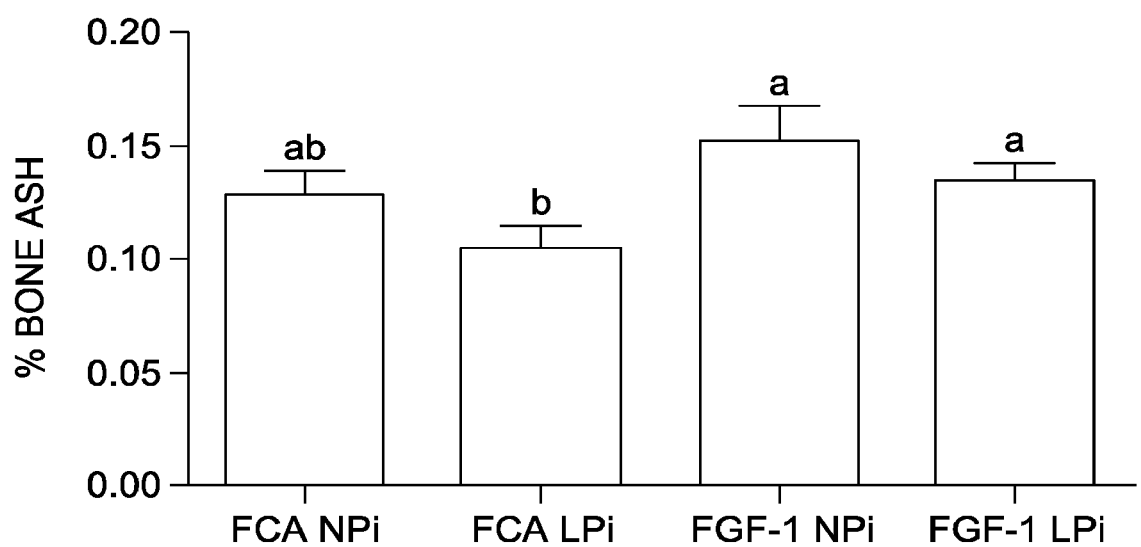
Figure 2B:
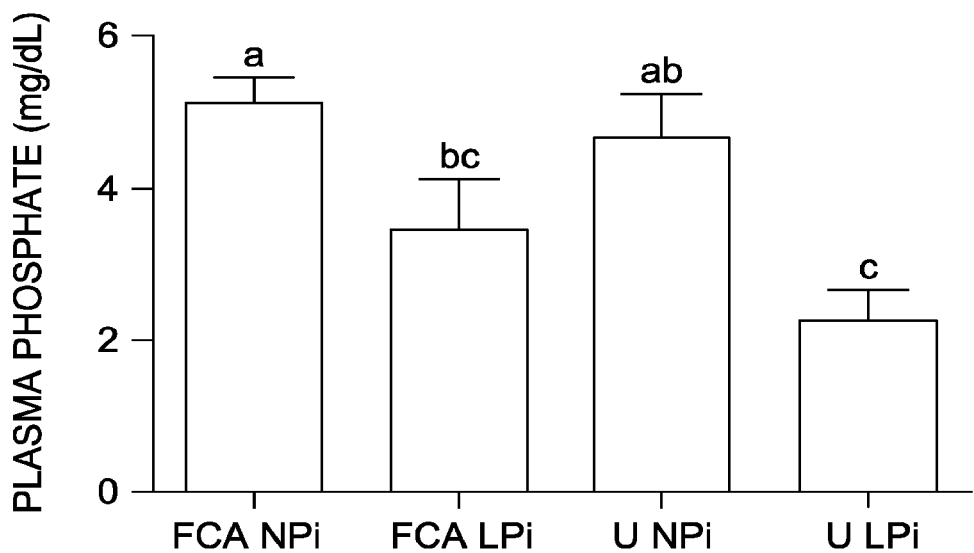
Figure 2C:
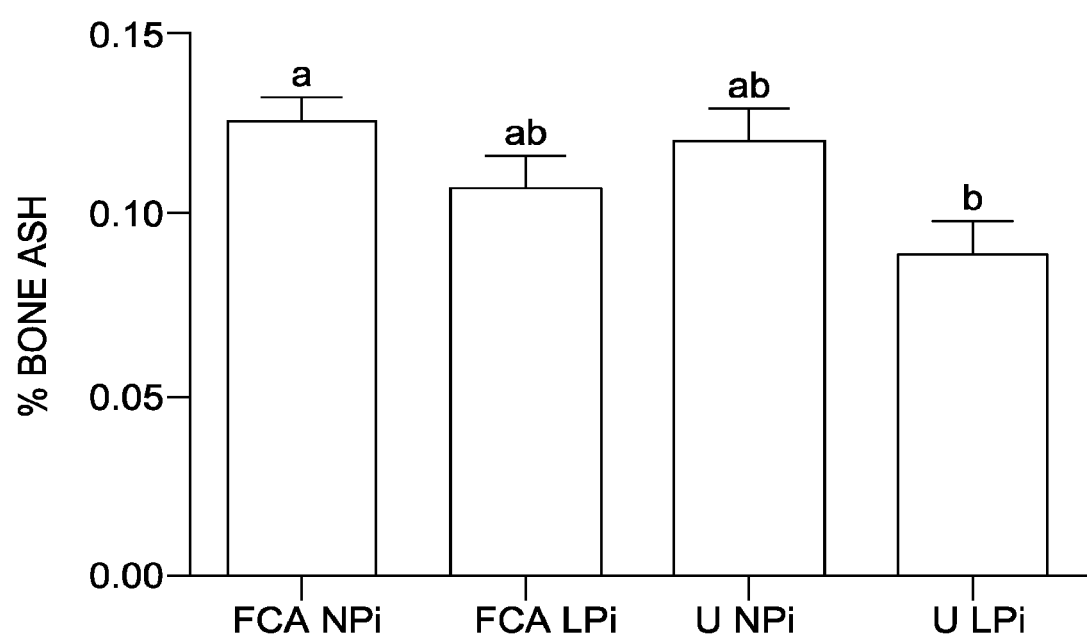

Chicks fed the phosphate deficient diet (main effect of diet) had reduced plasma phosphate (41% and 42% in experiments 1 and 2, respectively) when compared to chicks fed the diet adequate in phosphate. Anti-FGF-1 and anti-FGF-U was not effective at preventing the decline in plasma phosphate due to phosphate deficiency (FIGS. 1B, 2B, and Table 2).

Anti-FGF-1 was effective at preventing decreases in body weight (discussed above) and bone ash (discussed below) if chicks were fed a phosphate deficient diet. However, the reduction in blood phosphate associated with feeding a phosphate deficient diet was not prevented when the chicks received anti-FGF-1 antibodies. It is possible that the highest priority of the baby chick for plasma phosphate is growth and bone formation; hence, plasma phosphate is the last clinical indicator of inadequate phosphate to be restored. Indeed literature shows that plasma phosphate is the first or most sensitive indices of marginal levels of dietary needs to ascertain the actual phosphate requirements of chicks with anti-FGF-1 antibodies.

Effects of FGF-23 on Bone Ash Amounts

Bone ash was reduced 22% and 14% in experiments 1 and 2, respectively, when chicks were fed the phosphate deficient diet as compared to the phosphate adequate diet (main effect of diet, p=0.07 in experiment 1 and p=0.09 in experiment 2). The decrease in bone ash was prevented if chicks had passive anti-FGF-1, such that chicks on the phosphate deficient diet and passive anti-FGF-1 had bone ash equal to those fed the phosphate adequate diets. Anti-FGF-U did not prevent the decrease in bone ash associated with feeding a phosphate deficient diet. Anti-FGF-1, but not anti-FGF-U, increased bone ash (main effect of antibody, p=0.02) when compared to chick with the control antibody.

Phosphate is an essential mineral for the synthesis of bone. It seems reasonable that if blood phosphate was made available for bone formation through the inhibition of FGF-23, then bone ash would be increased. These data suggest that FGF-23, in response to dietary intake of phosphate, may result in the over secretion of phosphate essential for bone development. The inability of FGF-U to increase bone phosphate may be because it is ineffective at neutralizing plasma FGF-23. Anti-FGF-1's ability to result in normal bone ash on a phosphate deficient diet strongly suggests that the phosphate requirement of chicks, where FGF-23 is neutralized, is considerably lower than animal with intact FGF-23. Unlike wild birds, where seeds and insects can vary widely in their available phosphate content, birds raised under agricultural conditions have a constant supply of dietary phosphate. In the wild type diet, birds need a mechanism for excreting excess phosphate. In contrast, phosphate consumption of domestically fed animals can be rigidly controlled through diet formulation. Hence, one could question the value of FGF-23 in the domestic fowl since it may over excrete blood phosphate and block phosphate absorption.

Conclusion

Results of the experiments conducted suggest that altering the function of FGF-23 through maternally-derived antibody may reduce the dietary phosphate requirements of the baby chick. The ability to regulate the phosphate requirement through a neutralization of FGF-23 is epitope specific. Currently, the poultry industry uses 0.4 million tons of feed phosphate at a cost of $400 million in the United States alone. If a vaccine could be developed that reduced the use of a limited supply of feed phosphate, and decreased the excretion of phosphate in the environment, a cost-effective solution for phosphate pollution of surface water would be available.

Example 2

In this Example, the effect of altering the function of FGF-23 through maternally-derived antibody on the dietary phosphate requirements of baby chicks was analyzed.

Peptide Antibody Production: Conjugation and Injection

Figure 3:
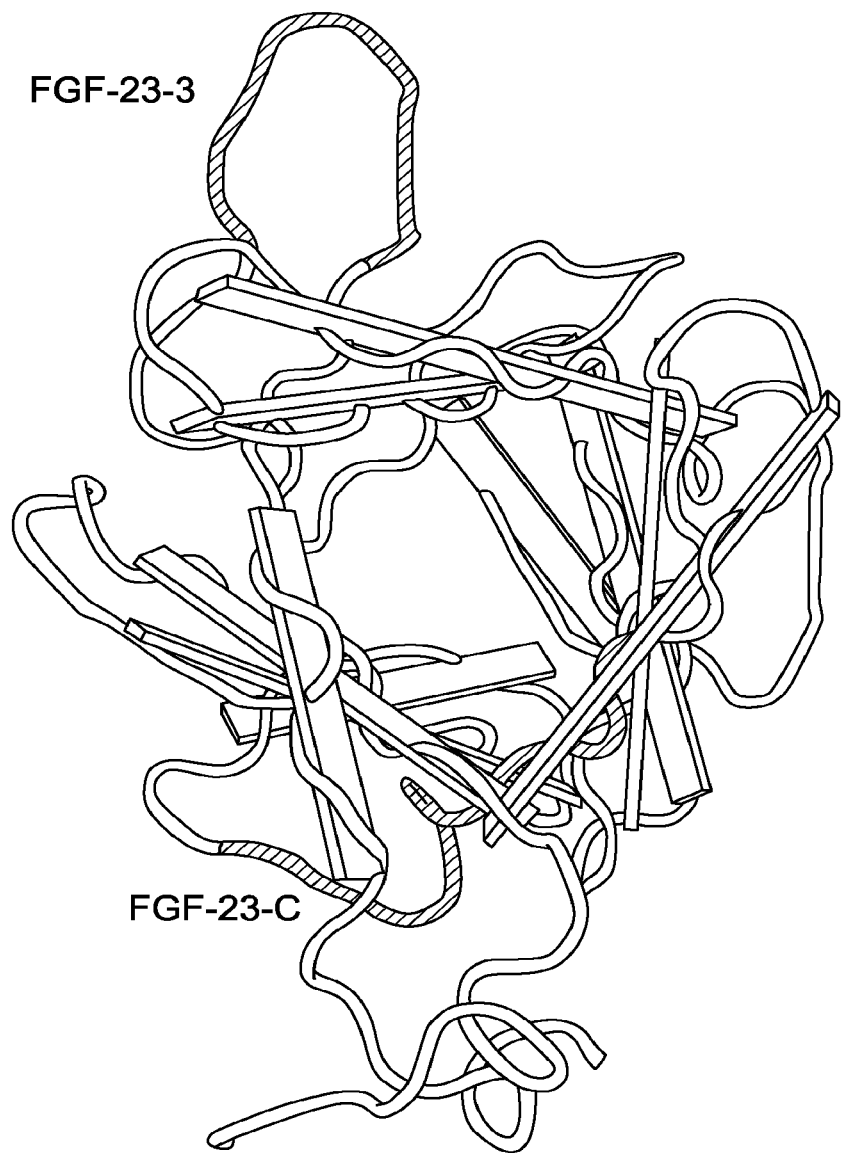
FIG. 3 is a diagram of two epitopes of FGF-23 (FGF-23-3; SEQ ID NO: 12 and FGF-23-C; SEQ ID NO: 46) used in Example 2.

Two epitopes of FGF-23, FGF-23-C(SEQ ID NO:46 (QTIYSALMI)) and FGF-23-3 (SEQ ID NO:12) shown in FIG. 3, were used for this Example. These peptides were individually conjugated to bovine gamma globulin (BgG, Sigma, St. Louis, Mo.) using glutaraldehyde conjugation similar to Example 1. Briefly, 2 mg of the carrier protein, BgG, was dissolved in 0.1 molar acetate buffer 2 mg of each peptide was then added to the buffer (1:1 peptide to carrier protein ratio), followed by 0.23 mL of 2 M glutaraldehyde and allowed to conjugate for 3 h at room temperature. The reaction was stopped with 10 mg glycine for 1 h. Dialysis occurred overnight in 1 L PBS at room temperature using 6000-8000 molecular weight dialysis tubing. Three hens per peptide were injected using 0.33 mg/hen/injection and yolks were freeze-dried for subsequent antibody analyses.

Enzyme-Linked Immunosorbent Assay (ELISA)

ELISA was utilized to demonstrate the presence of the anti-FGF-23 peptide antibodies in the yolks of eggs laid by vaccinated hens. Indirect ELISA methods were utilized except the antigen coated was 100 µg/plate of ovalbumin (OVA) or peptide-specific (FGF-23-3 or FGF-23-C) OVA conjugate, and blocking was accomplished using a non-protein blocking buffer (175 µl/well, Pierce Scientific, Rockford, Ill.). A second ELISA was run as described above, except native FGF-23 (human recombinant, Adipogen, San Diego, Calif.) or ovalbumin (OVA, Pierce Scientific, Rockford, Ill.) was used to coat the plate overnight (0.5 mg/mL) instead of an OVA-peptide conjugate. After blocking, antibodies to FGF-23-3, FGF-23-C, or FCA were incubated overnight at 1:1000 dilution and secondary antibody, substrate, and stop solution were all applied as described above. Primary antibodies applied to OVA were used as blanks (negative control; indicator of non specific binding).

Experimental Animal Population

Single Comb White Leghorn laying hens injected with the above mentioned FGF-23 peptide conjugates or FCA control were artificially inseminated once a week for two consecutive weeks with pooled New Hampshire rooster semen after 21 days following the primary injection or within 2 months of any booster injection used. Fertile eggs were incubated for 21 days, hatched, divided into groups based on the hens' peptide injection treatment, and assigned to one of two diets (Table 4): Diet 1) Basal: no added dietary phosphate (phosphate deficient with 0.13% available inorganic phosphorus and 0.27% unavailable phytate phosphorus, where the chick requirement=0.40% available phosphorus), Diet 2) Basal+ calcium and phosphorus in a balance ratio of 2:1 to meet dietary requirements. Chicks per treatment varied due to number of fertile eggs laid, set, and hatched per hen within each treatment group (see results for n/group). On day 14 on the experimental diets, chicks were weighed, bled for the determination of plasma phosphate, and the tibiotarsi were collected from euthanized chicks for bone ash determination. To determine bone ash, bones were ether extracted for 7 days to remove fat, dried, and then ashed in a muffle furnace for 24 hours at 600° C. (Pattison, Poultry Diseases 6*th* ed. Edinburgh, New York, N.Y., Elsevier/Butterworth-Heinemann 2008). Day 14 was used as the termination date to prevent severe phosphate deficient rickets and to assure continued presence of maternal antibody.

TABLE 4

Experimental Diet and Base Mix Composition

| Ingredient | Deficient Pi (%) | Adequate Pi (%) |
|---|---|---|
| Base Mix* | 96.60 | 96.60 |
| CaCO₃ | — | 0.96 |
| KH₂PO₄ | — | 1.20 |
| Sand | 3.40 | 1.24 |

| Base Mix* | g/100 g |
|---|---|
| Corn | 51.93 |
| Soy 48 | 40.50 |
| Corn Oil | 5.10 |
| CaCO₃ | 1.35 |
| Salt | 0.41 |
| DL-Methionine | 0.20 |
| Vit-Min Mix | 0.51 |

*Low and normal phosphate diets contained 0.52% and 0.66% total and 0.28 and 0.42 available phosphate (Pi), respectively.

Data Analysis

Data were analyzed by using two-way ANOVA as a 2×3 factorial (two diets and three antibody treatments) with SAS (SAS Institute, Inc., Cary, N.C.). Data were analyzed for main effects of diet, antibody and the diet X antibody interactions. Post-ANOVA analyses of mean treatment differences were conducted if the diet X antibody interaction was significant ($p<0.05$) using least squared differences (plasma phosphate and bone ash percentage). Data are shown as mean±standard error of the mean.

Results

Figure 4A:
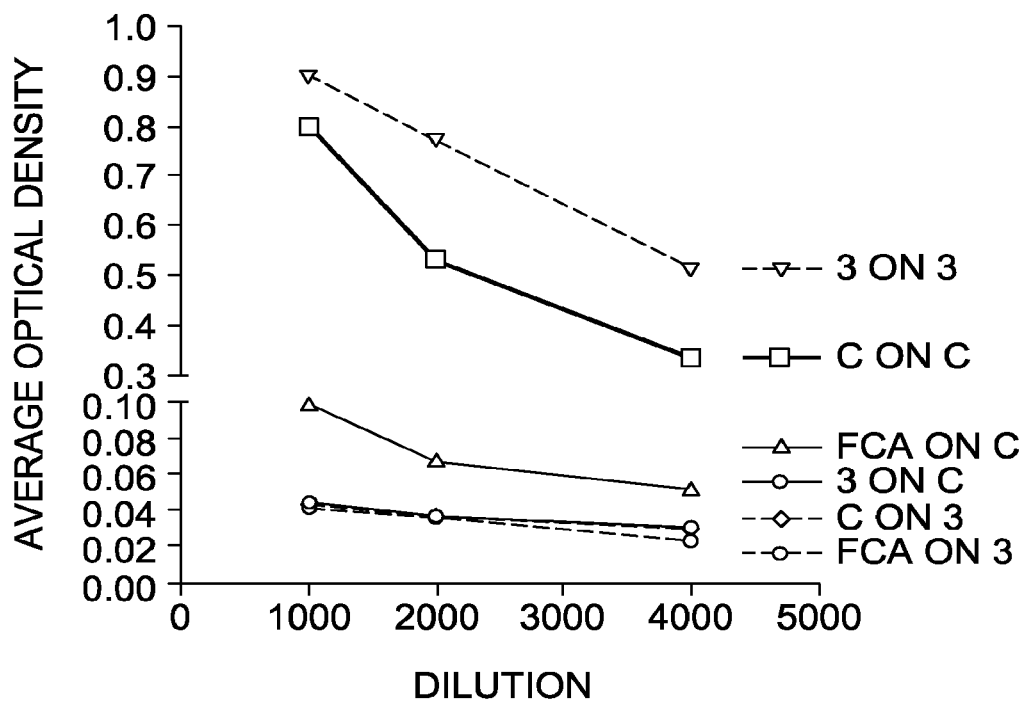
FIG. 4A is a graph depicting the specificity of antibodies used in Example 2 to their respective peptides. For example, "3 on 3" means antibody to FGF-23 peptide 3 (SEQ ID NO: 13) tested specifically for peptide 3 (SEQ ID NO: 13).
Figure 4B:
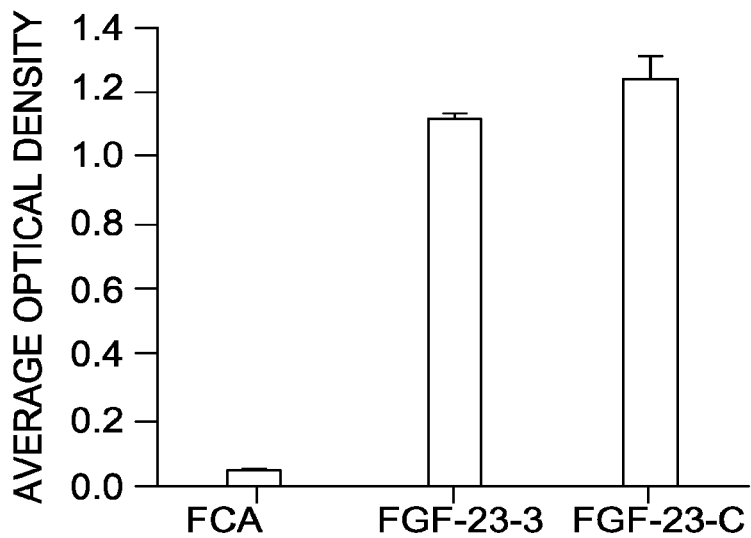
FIG. 4B is a graph depicting the specificity of antibodies used in Example 2 to their respective regions on the native human recombinant FGF-23 protein molecule.

Eggs collected from hens injected with control or their respective peptide conjugate were used in an ELISA assay to determine the transfer of peptide specific antibody to the egg yolk. Egg yolk antibody diluted as little as 1:1000 showed peptide specific binding when compared to control antibody (FCA) or nonspecific peptide conjugate antibody (i.e., FGF-23-C antibody on FGF-23-3 peptide or vice versa, FIG. 4A). When FGF-23 or FCA control antibodies were co-incubated with native FGF-23, both FGF-23 antibodies bound equally to native FGF-23, whereas control antibody did not (FIG. 4B).

Figure 5A:
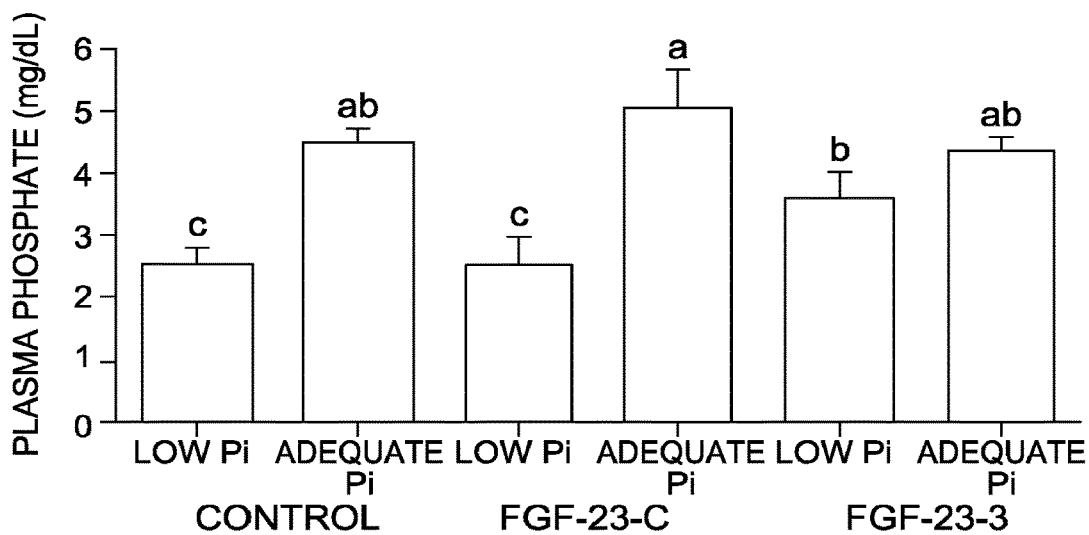
FIG. 5A is a graph depicting the plasma phosphate levels of chicks as analyzed in Example 2. Differing letters denote significant difference between low and normal phosphate within antibody treatment.

Following the artificial insemination procedures, eggs were collected from the control and FGF-23 vaccinated hens. A total of 30, 41, and 39 eggs were collected from the hens injected with the control, FGF-23-C, and FGF-23-3, respectively. No differences in the percent egg fertility and hatch of fertile eggs was observed as a result of vaccine treatment. All chicks within a vaccine treatment group were divided equally and assigned to either the low or adequate phosphate diet: FCA control, 10 chicks each for low and adequate phosphate diets; FGF-23-C, 12 and 11 chicks for low and adequate phosphate diet, respectively; and FGF-23-3, 18 chicks each for the low and adequate phosphate diet. After 2 weeks on the dietary treatments, chicks fed the adequate phosphate diet across all vaccine treatment groups had similar levels of plasma phosphate; whereas those fed the low phosphate diet had dissimilar plasma phosphate (diet X vaccine interaction $p<0.027$, FIG. 5A).

Control chicks on a low phosphate diet had 43% less plasma phosphate as compared to control chicks fed adequate phosphate ($p=0.0032$), anti-FGF-23-C chicks fed a low phosphate diet had a 50% reduction in plasma phosphate compared to anti-FGF-23-C chicks fed adequate phosphate ($p<0.0001$), whereas anti-FGF-23-3 chicks fed a low phosphate diet showed no significant decrease in plasma phosphate relative to anti-FGF-23-3 chicks fed adequate phosphate ($p=0.19$). Chicks with circulating anti-FGF-23-3 maternal antibodies and fed the low phosphate diet had plasma phosphate that was increased 31% and 33% above chicks fed the same diet but with circulating levels of control or anti-FGF-23-C antibodies, respectively ($p<0.05$). Hens producing control, anti-FGF-23-C and anti-FGF-23-3 antibodies had similar plasma phosphate levels (control=4.8 mg/dL±0.95; anti-FGF-23-C=4.4 mg/dL±0.98; anti-FGF-23-3=5.3 mg/dL±0.40).

Figure 5B:
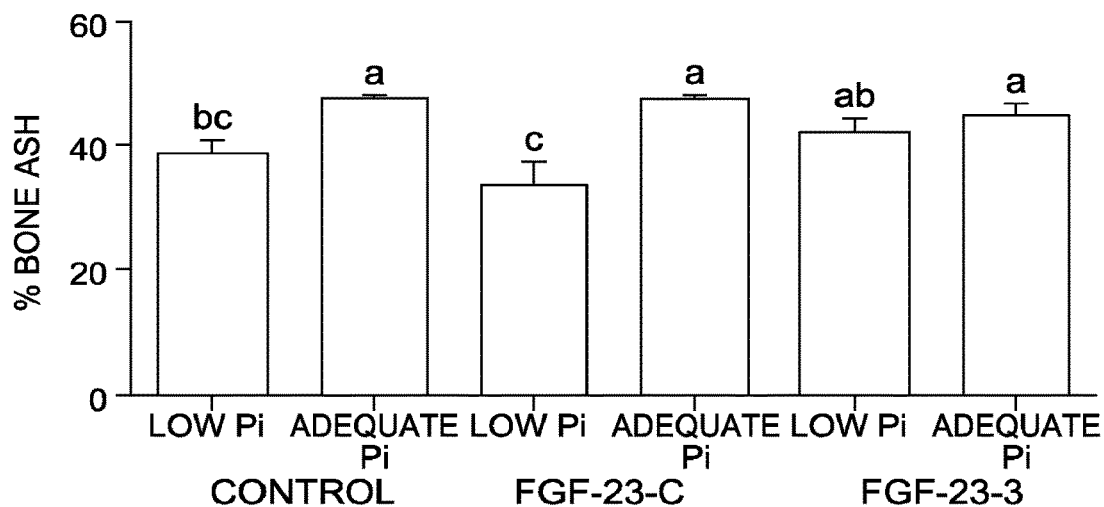
FIG. 5B is a graph depicting the bone ash percentage of chicks as analyzed in Example 2. Differing letters denote significant difference between low and normal phosphate within antibody treatment. Diets contained either deficient (low Pi) or adequate (adequate Pi) inorganic phosphate. Control is control antibody; FGF-23-C is antibody to SEQ ID NO: 46 and FGF-23 is antibody to SEQ ID NO: 12.

Percent bone ash was similar between vaccine treatment groups fed the phosphate adequate diet; however, a significant interaction between diet and maternal vaccination was observed ($p>0.05$, FIG. 5B). Control antibody and anti-FGF-23-C antibody chicks fed the phosphate deficient diet had a 21% ($p=0.014$) and 29% ($p<0.001$), respectively, reduction in bone ash percent when compared to relevant chicks fed adequate levels of phosphate. However, chicks with maternal anti-FGF23-3 antibody did not have a significantly reduced percent bone ash when fed a low phosphate diet and compared to anti-FGF-23-3 chicks fed adequate phosphate ($p=0.44$). Chicks with anti-FGF-23-3 maternal antibody and fed a low phosphate diet had an 11% ($p=0.19$) and 20% ($p=0.01$) increase in bone ash percent when compared to control and FGF-23-C chicks, respectively, fed the low phosphate diet.

Figure 5C:
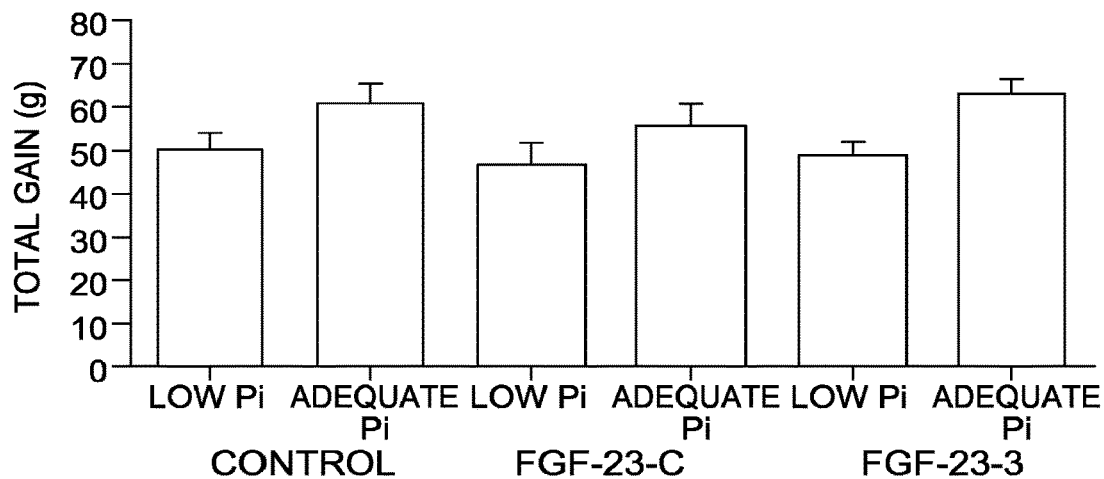
FIG. 5C is a graph depicting the total weight gain (grams) of chicks from hens vaccinated to induce the passive transfer of anti-FGF-23 antibodies to the chicks as analyzed in Example 2.

While chicks fed low phosphate had decreased weight gain regardless of maternal antibody type (main effect of diet, $p=0.0006$), there was no protection against decreased weight gain due to maternal antibody source (interaction of diet X maternal antibody, $p=0.65$, FIG. 5C).

Conclusion

Chicks with circulatory anti-FGF-23-3 antibody and fed adequate levels of phosphate did not have increased blood phosphate levels when compared to control fed chicks. In addition, hens that were injected with FGF-23-3 (the peptide associated with reduced phosphate requirements in the progeny) appeared to have normal plasma phosphate levels and health was not compromised as a result of the vaccine. These results suggest that neutralizing antibodies to FGF-23, such as through vaccination of the peptide of SEQ ID NO:12, may reduce the dietary phosphate requirements of the baby chicks.

Example 3

In this Example, the effect of altering the function of FGF-23 through maternally-derived antibody on the dietary phosphate requirements of baby chicks was analyzed.

The antibody to the FGF-23 peptide, FGF-1 (SEQ ID NO:1), was prepared and injected into three hens as described in Example 2. Separately, three hens were treated with control FCA. The hens were then inseminated three weeks post-injection, and eggs were collected for two weeks and set for incubation.

Hatched chicks were put on either a normal or low phosphate diet (see Table 5) on the day of hatching and allowed to grow for two weeks.

TABLE 5

Experimental Diets

| Ingredient | Deficient Pi (%) | Adequate Pi (%) |
|---|---|---|
| Base Mix* | 96.60 | 96.60 |
| CaCO₃ | 0.48 | 0.96 |
| KH₂PO₄ | 0.6 | 1.20 |
| Sand | 2.32 | 1.24 |

TABLE 5-continued

| Experimental Diets | |
|---|---|
| Base Mix* | g/100 g |
| Corn | 51.93 |
| Soy 48 | 40.50 |
| Corn Oil | 5.10 |
| CaCO$_3$ | 1.35 |
| Salt | 0.41 |
| DL-Methionine | 0.20 |
| Vit-Min Mix | 0.51 |

*Low and normal phosphate diets contained 0.52% and 0.66% total and 0.28 and 0.42 available phosphate (Pi), respectively.

Figure 6:
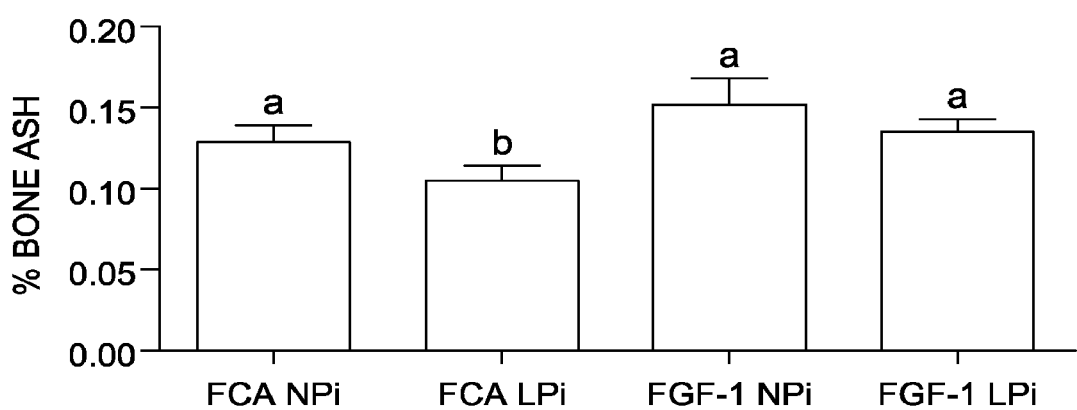
FIG. 6 is a graph depicting the bone ash percentage of chicks as analyzed in Example 3. Differing letters denote significant difference at $p<0.05$.

Bone ash was measured as in Example 2. As shown in FIG. 6, chicks fed a low phosphate diet in the presence of FGF-1 were significantly different from FCA control chicks fed a low phosphate diet, but not different than FCA or FGF-1 chicks fed a normal phosphate diet (p<0.05).

Example 4

In this Example, the effect of altering the function of FGF-23 through maternally-derived antibodies on the dietary phosphate requirements of the baby chicks was analyzed.

Antibodies to the following FGF-23 peptides, FGF-2 (SEQ ID NO:7); FGF-3 (SEQ ID NO:12); T (SEQ ID NO:20); W (SEQ ID NO:16) and FGF-C(SEQ ID NO:46), were prepared and injected into hens as described in Example 2. Three hens per peptide were treated. Three hens were separately treated with control FCA. The hens were then inseminated three weeks post-injection, and eggs were collected for two weeks and set for incubation.

Hatched chicks were put on either a normal or low phosphate diet (see Table 6) on the day of hatching and allowed to grow for two weeks.

TABLE 6

| Experimental Diets | | |
|---|---|---|
| Ingredient | Deficient Pi (%) | Adequate Pi (%) |
| Base Mix* | 96.60 | 96.60 |
| CaCO$_3$ | 0.48 | 0.96 |
| KH$_2$PO$_4$ | 0.6 | 1.20 |
| Sand | 2.32 | 1.24 |

| Base Mix* | g/100 g |
|---|---|
| Corn | 51.93 |
| Soy 48 | 40.50 |
| Corn Oil | 5.10 |
| CaCO$_3$ | 1.35 |
| Salt | 0.41 |
| DL-Methionine | 0.20 |
| Vit-Min Mix | 0.51 |

*Low and normal phosphate diets contained 0.52% and 0.66% total and 0.28 and 0.42 available phosphate (Pi), respectively.

Figure 7:
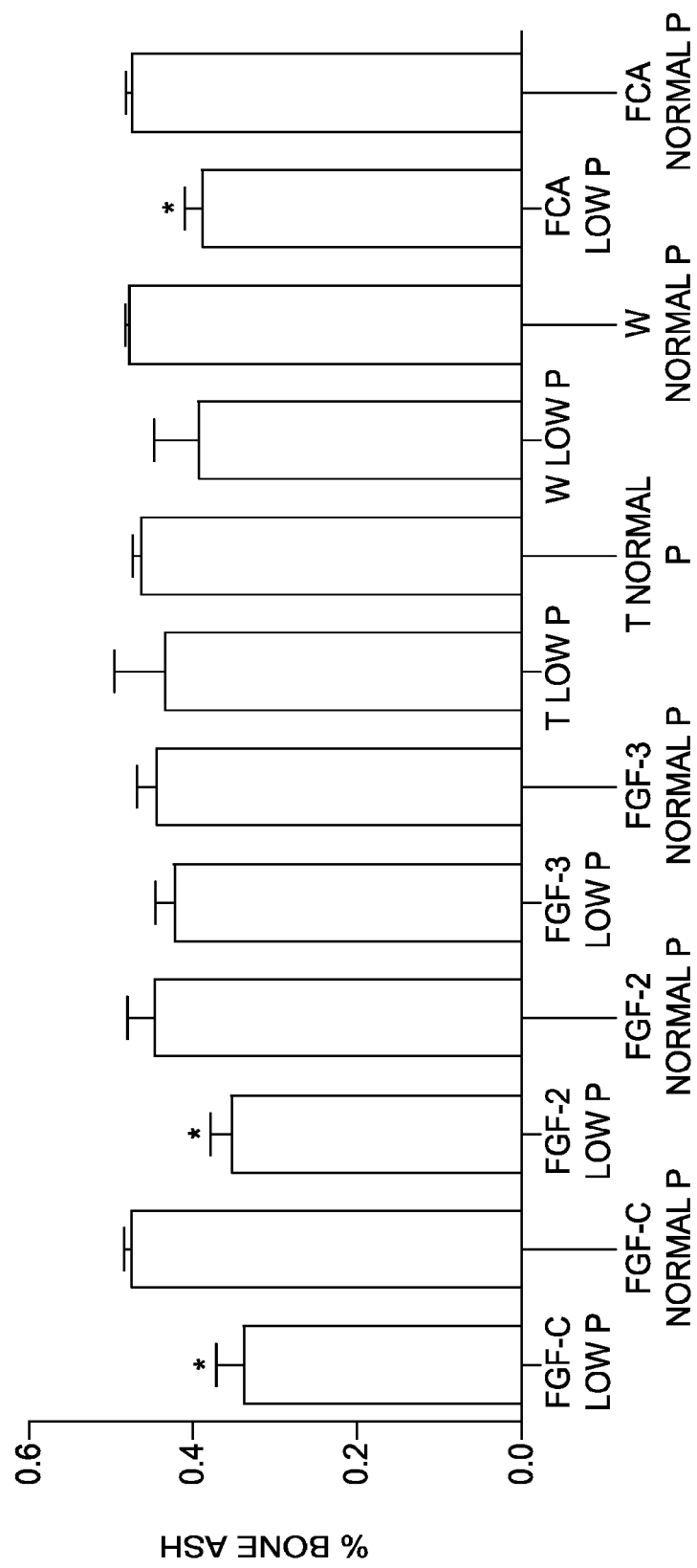
FIG. 7 is a graph depicting the bone ash percentage of chicks as analyzed in Example 4. * indicates significant difference between low and normal phosphate within antibody treatment. Low P and Normal P are diets of chicks fed deficient or adequate diets in inorganic phosphate, respectively. FGF-C, FGF-2, FGF-3, T, and W are passively transferred antibodies to SEQ ID NOS: 46, 7, 12, 20 and 16, respectively.

Bone ash, weight gain, and plasma phosphate were measured as in Example 2. As shown in FIG. 7, chicks fed high phosphate diets consistently had higher bone ash percentages than chicks of the same treatment fed low phosphate diets (main effect of diet, p<0.0001). Feeding T and FGF-3 chicks low phosphate diets only resulted in non-significant 6.5% and 6.6% decreases in bone ash as compared to T and FGF-3 chicks fed a normal phosphate diet (p=0.50). The FCA control chicks had a significant 20.8% decrease in bone ash, as expected (p=0.03). Moreover W chicks had 11.36% decrease in bone ash, FGF-C chicks had a 30% decrease, and FGF-2 chicks showed a 22.2% decrease, as compared to their respective normal phosphate-fed groups (p=0.19, p=0.0038, p=0.03, respectively). Overall, the antibodies to peptides W, FGF-3, and T reduced the bone mass lost from a low phosphate diet, but FGF-3 and T exhibited the best success in doing so.

Figure 8:
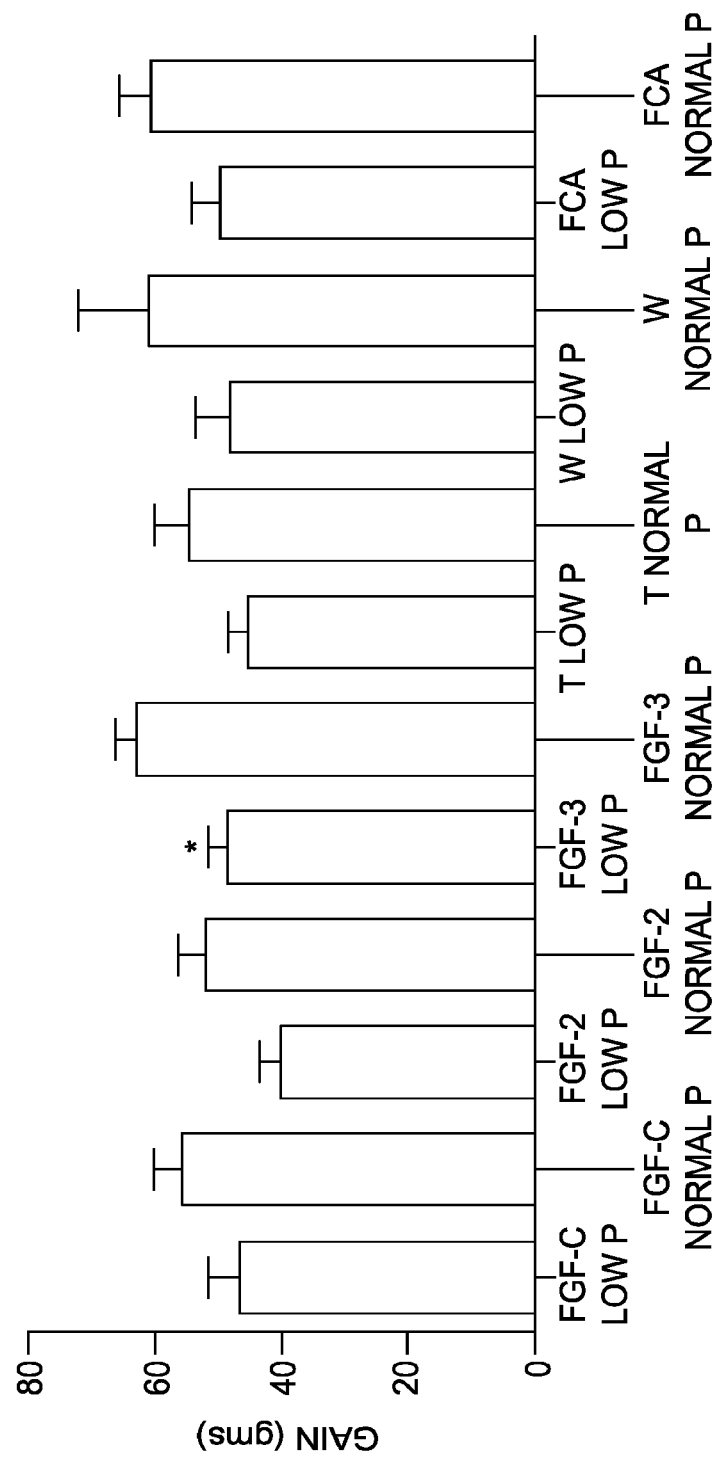
FIG. 8 is a graph depicting the total weight gain (grams) of chicks from hens vaccinated to induce the passive transfer of anti-FGF-23 antibodies to the chicks as analyzed in Example 4. * denotes significant difference between low and normal phosphate within antibody treatment. Low P and Normal P are diets of chicks fed deficient or adequate diets in inorganic phosphate, respectively. FGF-C, FGF-2, FGF-3, T, and W are passively transferred antibodies to SEQ ID NOS: 46, 7, 12, 20 and 16, respectively.

As shown in FIG. 8, feeding FGF-3 chicks a low phosphate diet resulted in a significant 25.14% decrease in final body weight versus normal phosphate (p=0.0008). Further, FCA control chicks fed a low phosphate diet did not have significantly reduced body weight gain as compared to normal phosphate fed chicks, but their weights were overall reduced by 16.7% (p=0.07).

Figure 9:
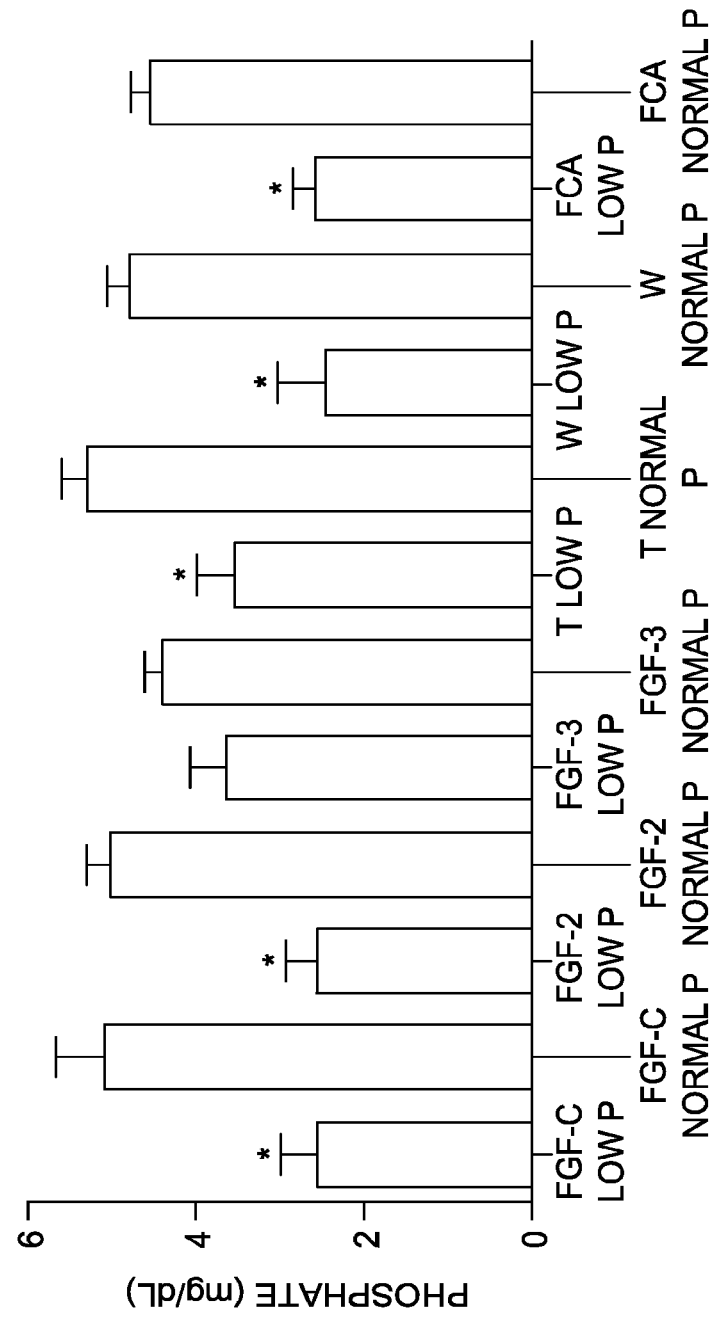
FIG. 9 is a graph depicting the plasma phosphate levels of chicks vaccinated to induce the passive transfer of anti-FGF-23 antibodies to the chicks as analyzed in Example 4. * indicates significant difference between low and normal phosphate within antibody treatment. Low P and Normal P are diets of chicks fed deficient or adequate diets in inorganic phosphate, respectively. FGF-C, FGF-2, FGF-3, T, and W are passively transferred antibodies to SEQ ID NOS: 46, 7, 12, 20 and 16, respectively.

As shown in FIG. 9, FCF-C and FCF-2 chicks fed a low phosphate diet had the largest percent decreases in plasma phosphate levels, with 56.59% and 46.5% decreases, respectively (p<0.0001). FGF-3 chicks fed low phosphate diets showed the smallest decrease in plasma phosphate levels, with only 13.69% (p=0.1525). T and W had 32.04% and 26.15% decreases, respectively, versus normal phosphate (p<0.003). The FCA control chicks fed low phosphate diets showed a 42.51% decrease in plasma phosphate levels (p=0.0011), which was substantially more than a majority of the treated chicks.

Conclusion

As shown in this Example, maternal antibody can be used to neutralize FGF-23 and decrease the phosphate requirements necessary for chicks to grow efficiently by reducing the amount of phosphate an animal excretes. Further, minimal differences are observed in bone ash percentages in the FGF-3 and T antibody groups, indicating that the chicks were able to prevent the loss of enough phosphate to maintain bone ash even on the low phosphate diets.

Example 5

In this Example, the effect of altering the function of FGF-23 through antibodies on the dietary phosphate requirements of the baby chicks was analyzed.

Antibodies to FGF-23 peptides, Chicken T (SEQ ID NO:21); Chicken FGF-3 (SEQ ID NO: 13); FGF-3 (SEQ ID NO:12); and T (SEQ ID NO:20), were prepared and injected into three hens as described in Example 2. The hens were then inseminated three weeks post-injection, and eggs were collected for two weeks and set for incubation.

Hatched chicks were put on either a normal or low phosphate diet (see Table 7) on the day of hatching and allowed to grow for two weeks.

TABLE 7

| Experimental Diets | | |
|---|---|---|
| Ingredient | Deficient Pi (%) | Adequate Pi (%) |
| Base Mix* | 96.60 | 96.60 |
| CaCO$_3$ | 0.48 | 0.96 |
| KH$_2$PO$_4$ | 0.6 | 1.20 |
| Sand | 2.32 | 1.24 |

| Base Mix* | g/100 g |
|---|---|
| Corn | 51.93 |
| Soy 48 | 40.50 |
| Corn Oil | 5.10 |

TABLE 7-continued

| Experimental Diets | |
|---|---|
| CaCO$_3$ | 1.35 |
| Salt | 0.41 |
| DL-Methionine | 0.20 |
| Vit-Min Mix | 0.51 |

*Low and normal phosphate diets contained 0.52% and 0.66% total and 0.28 and 0.42 available phosphate (Pi), respectively.

Figure 10:
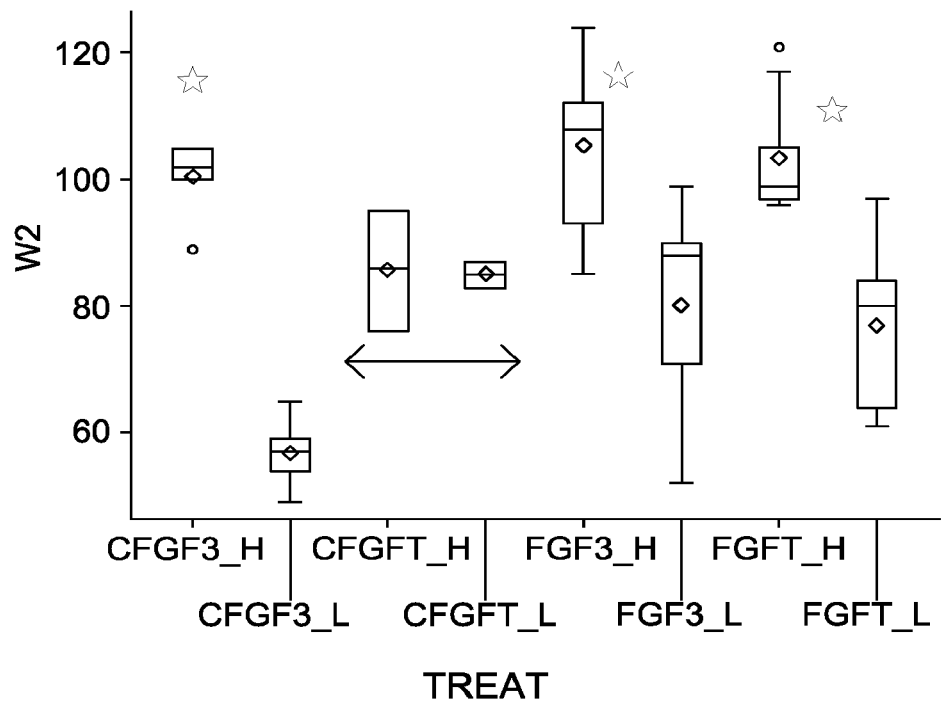
FIG. 10 is a graph depicting the two-week weight gain (W2) in grams of chicks from hens vaccinated to induce the passive transfer of anti-FGF-23 antibodies to the chicks as analyzed in Example 5. * indicates significant difference between low and normal phosphate within antibody treatment. H and L represent chicks fed diet adequate (H) or deficient (L) levels of inorganic phosphate. CFGF3, CFGFT, FGF3 and FGFT represent passively transferred antibodies to peptides of SEQ ID NOS: 13, 21, 12 and 20, respectively.

As shown in FIG. 10, weight reduction due to phosphate deficiency was protected with antibody to Chicken T, FGF-3, and T, but not Chicken FGF-3.

Example 6

In this Example, the effect of altering the function of FGF-23 through antibodies on the plasma phosphate levels of the baby chicks was analyzed.

Antibodies to FGF-23 peptides, Chicken FGF-3 (SEQ ID NO:13); FGF-3 (SEQ ID NO:12); Chicken T (SEQ ID NO:21); and T (SEQ ID NO:20), were prepared and injected into three hens as described in Example 2. The hens were then inseminated three weeks post-injection, and eggs were collected for two weeks and set for incubation.

Hatched chicks were put on either a normal or low phosphate diet (see Table 8) on the day of hatching and allowed to grow for two weeks.

TABLE 8

| Experimental Diets | | |
|---|---|---|
| Ingredient | Deficient Pi (%) | Adequate Pi (%) |
| Base Mix* | 96.60 | 96.60 |
| CaCO$_3$ | 0.48 | 0.96 |
| KH$_2$PO$_4$ | 0.6 | 1.20 |
| Sand | 2.32 | 1.24 |
| Base Mix* | g/100 g | |
| Corn | 51.93 | |
| Soy 48 | 40.50 | |
| Corn Oil | 5.10 | |
| CaCO$_3$ | 1.35 | |
| Salt | 0.41 | |
| DL-Methionine | 0.20 | |
| Vit-Min Mix | 0.51 | |

*Low and normal phosphate diets contained 0.52% and 0.66% total and 0.28 and 0.42 available phosphate (Pi), respectively.

Figure 11:
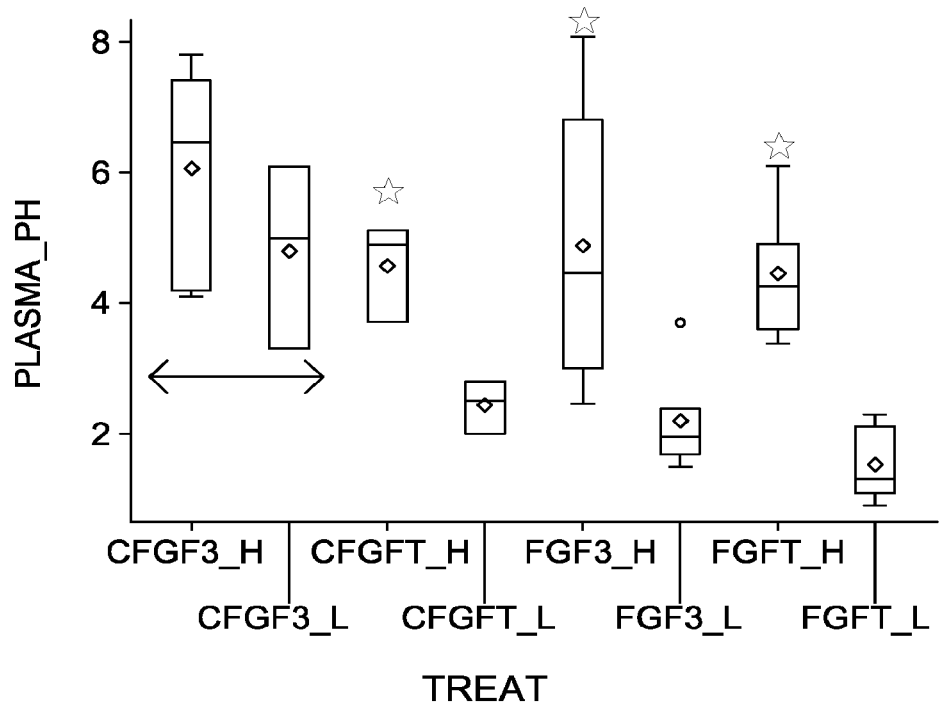
FIG. 11 is a graph depicting the plasma phosphate levels of chicks from hens vaccinated to induce the passive transfer of anti-FGF-23 antibodies to the chicks as analyzed in Example 6. * indicates significant difference between low and normal phosphate within antibody treatment. H and L represent chicks fed diet adequate (H) or deficient (L) levels of inorganic phosphate. CFGF3, CFGFT, FGF3 and FGFT represent passively transferred antibodies to peptides of SEQ ID NOS: 13, 21, 12 and 20, respectively.

As shown in FIG. 11, Chicken FGF-3 provided protection against decreased plasma phosphate during phosphate deficient feed.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An FGF-23 epitope polypeptide consisting of an amino acid sequence selected from the group consisting of SEQ ID NO:46, SEQ ID NO: 47, and SEQ ID NO:48, wherein the FGF-23 epitope polypeptide is conjugated to a carrier protein.

2. The FGF-23 epitope polypeptide of claim 1, wherein the carrier protein is selected from the group consisting of bovine gamma globulin, FGF-23, bovine serum albumin, keyhole limpet hemocyanin, and ovalbumin.

3. A vaccine composition comprising the FGF-23 epitope polypeptide of claim 1, wherein the vaccine composition is an injectable composition comprising an immunological adjuvant.

4. The vaccine composition of claim 3, wherein the carrier protein is selected from the group consisting of bovine gamma globulin, FGF-23, bovine serum albumin, keyhole limpet hemocyanin, and ovalbumin.

5. A method of reducing dietary phosphate requirements of livestock and livestock offspring, the method comprising inducing production of a maternal antibody by introducing the FGF-23 epitope polypeptide of claim 1 into a fertile livestock female, and
fertilizing at least one egg of the livestock, wherein said maternal antibody is transferred to the livestock offspring via egg yolk, placenta or colostrum, thereby altering the livestock offspring's metabolism of the dietary nutrient.

6. The method of claim 5, wherein the dietary nutrient is phosphate.

7. The method of claim 5, wherein the conjugated vaccine is introduced into the livestock in an amount between about 50 micrograms and about 6 milligrams.

8. A method of altering phosphate metabolism in a livestock, the method comprising:
inducing production of an antibody by introducing the FGF-23 epitope polypeptide of claim 1 into the livestock.

9. The method of claim 8, wherein production of the antibody is induced by injecting the livestock with the FGF-23 epitope polypeptide.

10. The method of claim 8, further comprising feeding the livestock a diet comprising citric acid.

11. A method of eliciting an immune response in a livestock comprising introducing into the livestock an FGF-23 epitope polypeptide consisting of an amino acid sequence selected from the group consisting of SEQ ID NO:46, SEQ ID NO: 47, and SEQ ID NO:48, wherein the FGF-23 epitope polypeptide is conjugated to a carrier protein.

12. The method of claim 11, wherein the livestock is an avian.

13. The method of claim 11, wherein the livestock is a chicken, a turkey, a duck, a pheasant, a quail, a fish, a sheep, a swine, or a cow.

14. The method of claim 11, wherein introducing comprises injecting the livestock with the FGF-23 epitope polypeptide.

* * * * *

SEQUENCE LISTING

```
<160> NUMBER OF SEQ ID NOS: 48

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Val Asp Gly Ala Pro His Gln Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Asn Gly Val Pro His Gln Thr
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3
```

Val Asp Gly Ser Pro Gln Gln Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Val Arg Lys Ser Thr Ala Arg Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Thr Leu Glu Asn Gly Tyr Asp Val
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Leu Leu Glu Asn Asn Arg Asp Val
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Tyr Pro Asn Ala Ser Pro Leu Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Phe Pro Asn Ser Ser Pro Leu Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Tyr Pro Asp Thr Ser Pro Leu Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Tyr Pro Asn Ser Ser Pro Leu Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Ala Pro Asn Ala Ser Pro Leu Val
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Ala Phe Leu Pro Gly Met Asn Pro
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Val Phe Phe Pro Gly Met Asn Pro
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Ala Phe Leu Pro Gly Thr Asn Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Val Phe Val Val Gly Gln Asn Val

```
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Arg Asp Pro Leu Asn Val Leu Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Leu Asp Pro His Gln Ile Leu Val
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Asp Pro Leu Ser Val Leu Lys
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Ser Asp Pro His Arg Val Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Arg Arg His Thr Arg Ser Ala Glu
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

His Arg Asn Thr Arg Ser Ala Asp
1               5
```

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Arg Arg His Thr Arg Ser Ala His
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Arg His Thr Arg Ser Ala His Asp
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

His Arg Asp Lys Arg Asn Gln Val
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Gly Met Asn Pro Pro Pro Tyr Ser
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Gly Thr Asn Pro Pro Pro Tyr Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Gly Gln Asn Val Pro Gln Thr Ser
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Arg Asn Glu Ile Pro Leu Ile His
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Arg Asn Glu Ile Pro Leu Phe Arg
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Arg Asn Glu Ile Pro Leu Leu His
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Arg Asn Glu Ile Pro Leu Pro His
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Thr Asn Thr Val Pro Leu Glu Arg
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Ala Lys Arg Ala Phe Leu Pro Gly
1               5

```
<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Thr Lys Gln Val Phe Phe Pro Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Ser Arg Gln Val Phe Val Val Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Asn Thr Pro Ile Pro Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Phe Asn Thr Pro Glu Pro His Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ala Thr Ala Arg Pro Arg Arg
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Ala Ala Thr Ala Arg Pro Arg Arg
1               5

<210> SEQ ID NO 40
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 40

Leu Leu His Arg
1

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Thr Arg Ser Ala Glu Asp Asp Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Thr Arg Ser Ala Asp Val Asp Pro
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

Thr Arg Ser Ala His Asp Gly Gly
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Thr Arg Ser Ala His Asp Ser Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Lys Arg Asn Gln Val Val Asp Pro
1               5

<210> SEQ ID NO 46
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 46

Gln Thr Ile Tyr Ser Ala Leu Met Ile
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Gln Thr Val Tyr Ser Ala Leu Met Ile
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Arg Thr Ser Tyr Ser Val Ile Leu Leu
1               5
```